(12) United States Patent
Nihei et al.

(10) Patent No.: US 12,328,955 B2
(45) Date of Patent: Jun. 10, 2025

(54) THIN FILM AND METHOD FOR PRODUCING SAME, CIRCULARLY POLARIZED LIGHT DETECTION ELEMENT, DEVICE AND METHOD

(71) Applicant: JAPAN SCIENCE AND TECHNOLOGY AGENCY, Kawaguchi (JP)

(72) Inventors: Ayumi Nihei, Yokohama (JP); Tsutomu Miyasaka, Machida (JP)

(73) Assignee: JAPAN SCIENCE AND TECHNOLOGY AGENCY, Kawaguchi (JP)

( * ) Notice: Subject to any disclaimer, the term of this patent is extended or adjusted under 35 U.S.C. 154(b) by 463 days.

(21) Appl. No.: 17/998,203

(22) PCT Filed: May 25, 2021

(86) PCT No.: PCT/JP2021/019745
§ 371 (c)(1),
(2) Date: Nov. 8, 2022

(87) PCT Pub. No.: WO2021/241554
PCT Pub. Date: Dec. 2, 2021

(65) Prior Publication Data
US 2023/0231069 A1    Jul. 20, 2023

(30) Foreign Application Priority Data

May 28, 2020    (JP) ................ 2020-093727

(51) Int. Cl.
*H10K 50/86*    (2023.01)
*G01J 4/04*    (2006.01)
(Continued)

(52) U.S. Cl.
CPC ........... *H10F 30/00* (2025.01); *G01J 4/04* (2013.01); *H10K 71/12* (2023.02); *H10K 85/50* (2023.02)

(58) Field of Classification Search
CPC ................... H10K 59/8792; H10K 50/868
See application file for complete search history.

(56) References Cited

U.S. PATENT DOCUMENTS

| | | | |
|---|---|---|---|
| 2017/0276836 A1 | 9/2017 | Soci et al. | |
| 2020/0062740 A1 | 2/2020 | Dou et al. | |

(Continued)

FOREIGN PATENT DOCUMENTS

| | | | |
|---|---|---|---|
| CN | 110655914 A | 1/2020 | |
| CN | 110863246 A | 3/2020 | |

(Continued)

OTHER PUBLICATIONS

Notice of Allowance issued by the Japanese Patent Office on Dec. 5, 2023, for Japanese Application No. 2022-526569, and an English translation of the Notice (5 pages).

(Continued)

*Primary Examiner* — Benjamin P Sandvik
(74) *Attorney, Agent, or Firm* — Panitch Schwarze Belisario & Nadel LLP

(57) ABSTRACT

This thin film is a thin film for detecting circularly polarized light, and includes a plurality of inorganic layers constituting a layered structure and/or a plurality of inorganic chains (Continued)

constituting a chain structure, which are formed of a perovskite type substance, and chiral molecules incorporated in at least a part of a boundary part between the adjacent inorganic layers and/or between the inorganic chains, wherein the chiral molecules include only one of S-form chiral molecules and R-form chiral molecules or chiral molecules with a higher abundance proportion of one of S-form chiral molecules and R-form chiral molecules than an abundance proportion of the other of S-form chiral molecules and R-form chiral molecules, and wherein the crystal structure of the perovskite type substance is oriented in a predetermined direction.

19 Claims, 11 Drawing Sheets

(51) Int. Cl.
*H10F 30/00* (2025.01)
*H10K 71/12* (2023.01)
*H10K 85/50* (2023.01)

(56) References Cited

U.S. PATENT DOCUMENTS

| 2021/0217996 A1* | 7/2021 | Hamilton | H10K 85/50 |
| 2022/0251443 A1* | 8/2022 | Beard | H10K 50/868 |
| 2022/0326082 A1* | 10/2022 | Beard | H10K 85/221 |

FOREIGN PATENT DOCUMENTS

| JP | 2001021850 A | 1/2001 |
| KR | 1020190004942 A | 1/2019 |

OTHER PUBLICATIONS

Chen et al., "Circularly polarized light detection using chiral hybrid perovskite," Nature Communications, Apr. 26, 2019, vol. 10, Article No. 1927, 8 pages.

International Search Report (PCT/ISA/210) with English translation, and Written Opinion (PCT/ISA/237) mailed on Aug. 17, 2021, by the Japanese Patent Office as the International Searching Authority for International Application No. PCT/JP2021/019745.

Lu et al., "Spin-dependent charge transport through 2D chiral hybrid lead-iodide perovskites," Science Advances, Dec. 6, 2019, vol. 5, No. 12, 8 pages.

* cited by examiner

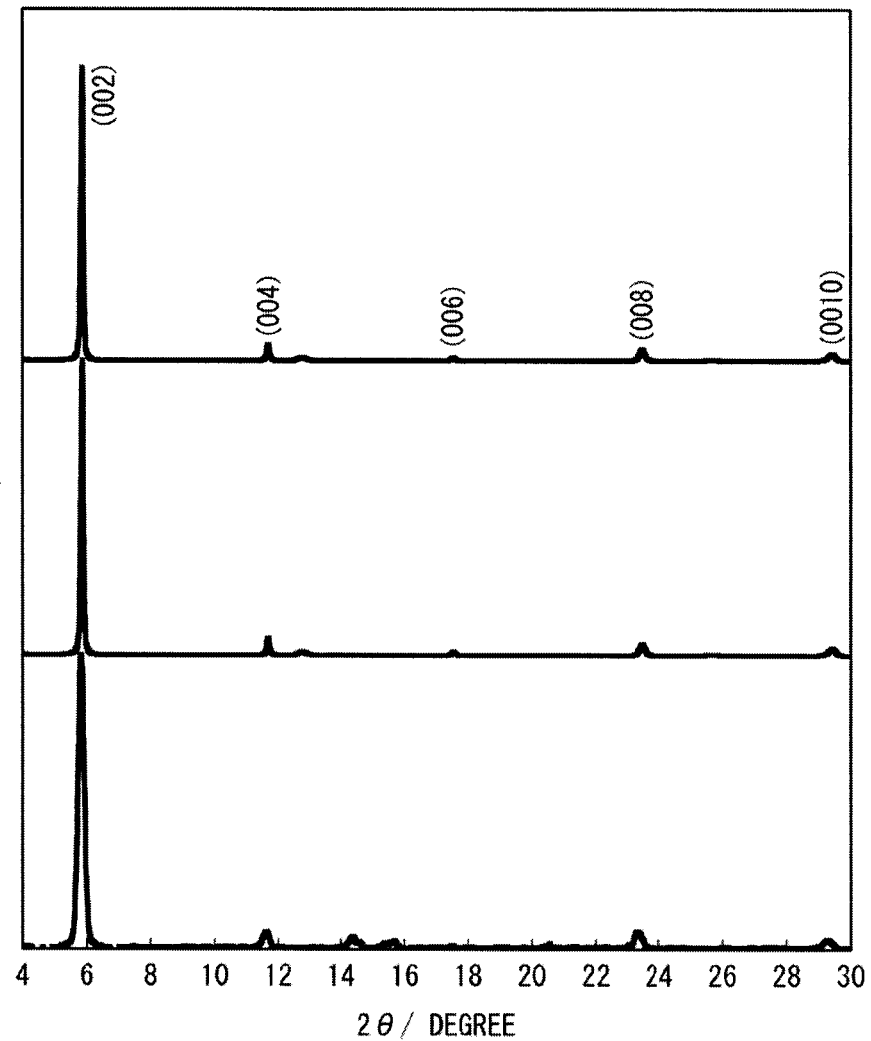

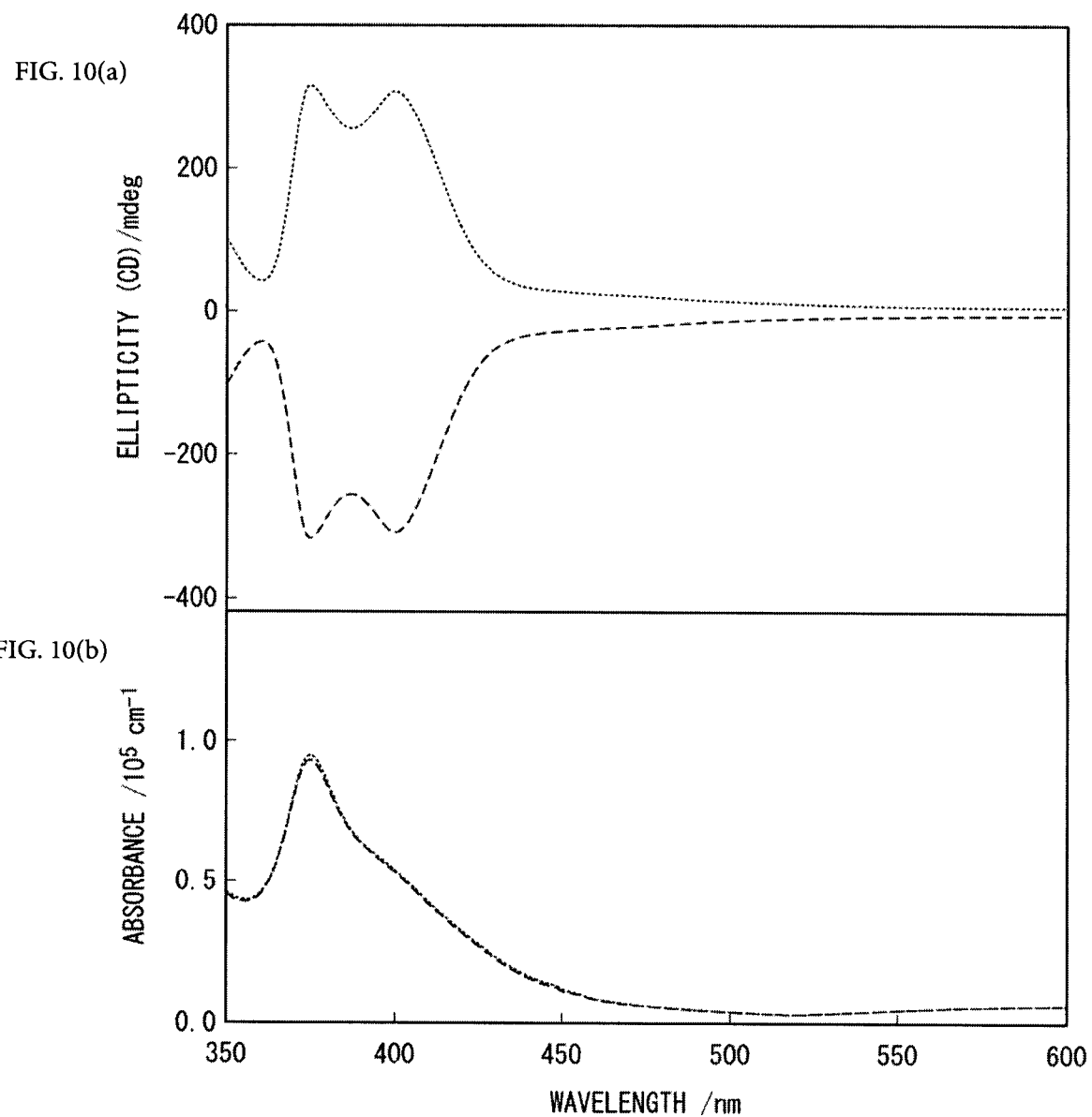

THIN FILM AND METHOD FOR PRODUCING SAME, CIRCULARLY POLARIZED LIGHT DETECTION ELEMENT, DEVICE AND METHOD

TECHNICAL FIELD

The present invention relates to a thin film, a method for producing the same, a circularly polarized light detection element, a device, and a method. Priority is claimed on Japanese Patent Application No. 2020-093727, filed May 28, 2020, the content of which is incorporated herein by reference.

BACKGROUND ART

Polarization image sensors that visualize information such as structures and properties of various objects using a polarization phenomenon are known. The polarization image sensor includes a polarizer array including a plurality of groups of four polarizers having different polarization directions and a photodiode array including a plurality of photodiodes arranged to face groups of the polarizers. A linearly polarized light signal that has passed through four polarizers belonging to the same group is converted into an electrical signal by a photodiode as information of one pixel and output. From the signal output from the linearly polarized light, three types of Stokes parameters can be calculated by combining the sum and difference of intensities of orthogonal polarization components, and the state of light transmitted can be quantified using them.

However, it is difficult to visualize the state of an object such as double refraction and stress distribution, which is seen when the object is bent, simply using three Stokes parameters obtained from linearly polarized light. It is known that these states can be visualized using Stokes parameters calculated from the intensity of circularly polarized light, and a technique for detecting circularly polarized light is desired. In addition, when circularly polarized light is detected with the above polarization image sensor, since a wavelength plate is additionally required, there is a problem that the sensitivity is significantly lowered. Therefore, a technique for directly detecting circularly polarized light is desired.

In Non Patent Literature 1, as a structure in which circularly polarized light in a wavelength range of around 400 nm is directly detected, a structure in which $(PbI_6)^{4-}$ (octahedron structure) is arranged one-dimensionally (that is, $(PbI_6)^{4-}$ that shares planes is arranged), and a chiral molecule (1-phenylethylamine) surrounds it is disclosed.

CITATION LIST

Non Patent Literature

[Non Patent Literature 1]
Chao Chen et al., Nature Communications, volume 10, Article number: 1927 (2019)

SUMMARY OF INVENTION

Technical Problem

Currently, in order to directly detect circularly polarized light, a new thin film that promotes a large chiral structure in the entire system and a method for producing the same are desired.

The present invention has been made in view of the above circumstances, and an object of the present invention is to provide a thin film that can directly detect circularly polarized light in a wide wavelength range, a method for producing the same, a circularly polarized light detection element including the thin film, a device, and a method.

Solution to Problem

In order to achieve the above object, the present invention includes the following aspects.
(1) A thin film according to one aspect of the present invention is a thin film for a detecting circularly polarized light, including: a plurality of inorganic layers constituting a layered structure and/or a plurality of inorganic chains constituting a chain structure, which are formed of a perovskite type substance; and chiral molecules incorporated in at least a part of a boundary part between the adjacent inorganic layers and/or between the inorganic chains, the chiral molecules including only one of S-form chiral molecules and R-form chiral molecules,
or chiral molecules with a higher abundance proportion of one of S-form chiral molecules and R-form chiral molecules than an abundance proportion of the other of the S-form chiral molecules and R-form chiral molecules, and the crystal structure of the perovskite type substance being oriented in a predetermined direction.
(2) In the thin film according to (1), preferably, an absorption intensity per unit thickness is 50,000 $cm^{-1}$ or more and 500,000 $cm^{-1}$ or less.
(3) In the thin film according to (1) or (2), preferably, a surface roughness Ra is 1 nm or more and 30 nm or less.
(4) In the thin film according to any one of (1) to (3), preferably, the chiral molecules form an organic layer at the boundary part, and the inorganic layer and the organic layer are alternately laminated and/or the chiral molecules surround the inorganic chains.
(5) In the thin film according to any one of (1) to (4), preferably, the chiral molecules are fixed to the inorganic layer and/or the inorganic chain.
(6) In the thin film according to any one of (1) to (5), preferably, the chiral molecules are bonded to the inorganic layer and/or the inorganic chain via a functional group covalently bonded to asymmetric carbon atoms constituting the chiral molecules.
(7) In the thin film according to (6), preferably, the functional group is a substituent that is able to have a charge, the substituent and the perovskite type substance form a bond via a halogen ion, which fixes the chiral molecule to the inorganic layer and/or the inorganic chain.
(8) In the thin film according to any one of (1) to (7), preferably, the perovskite type substance and the chiral molecules constitute a compound $A_2BX_4$ and/or $ABX_3$ composed of three types of ions A, B, and X, and the thin film may include a structure in which the ion B and the ion X form a plurality of units having an octahedron structure, and the octahedron structures of the adjacent units share one vertex and/or plane.
(9) The thin film according to (8) may include a plurality of inorganic layers constituting a layered structure, the perovskite type substance and the chiral molecules may constitute a compound $A_2BX_4$ composed of three types of ions A, B, and X, and the thin film may include a structure in which the ion B and the ion X form a plurality of units having an octahedron structure, and the octahedron structures of the adjacent units share one vertex.

(10) The thin film according to (8) may include a plurality of inorganic chains constituting a chain structure, the perovskite type substance and the chiral molecules may constitute a compound $ABX_3$ composed of three types of ions A, B, and X, and the thin film may include a structure in which the ion B and the ion X form a plurality of units having an octahedron structure, and the octahedron structures of the adjacent units share one plane.

(11) In the thin film according to any one of (8) to (10), preferably, the ion A is an aromatic compound containing an ethylammonium ion, the ion B is a lead ion or a tin ion, and the ion X is a halogen ion.

(12) A method for producing a thin film according to one aspect of the present invention is a method for producing the thin film according to any one of (1) to (11), including a first step in which a precursor of the perovskite type substance which is a raw material of the thin film, the chiral molecules, and an organic halide that is able to be sublimated by heating and reacts with some of elements constituting the perovskite type substance are dissolved in a solvent; a second step in which a solution obtained in the first step is applied onto a substrate using a spin coating method to form an untreated coating film on the substrate; and a third step in which the untreated coating film is heated to sublimate the organic halide contained in the untreated coating film.

(13) In the method for producing a thin film according to (12), preferably, the precursor of the perovskite type substance is a lead halide, and the organic halide is methylammonium halide or formamidinium halide.

(14) In the method for producing a thin film according to (13), preferably, a halogen atom contained in the lead halide and the organic halide is any of a bromine atom, a chlorine atom, and an iodine atom.

(15) A circularly polarized light detection element according to one aspect of the present invention includes the thin film according to any one of (1) to (11).

(16) In the circularly polarized light detection element according to (15), preferably, a negative electrode layer, the thin film, and a positive electrode layer are laminated in that order, and at least one of the negative electrode layer and the positive electrode layer has light transmitting properties.

(17) A device according to one aspect of the present invention includes the circularly polarized light detection element according to (15) or (16).

(18) A method according to one aspect of the present invention is a method for inducing an R- or S-arranged chiral structure for a perovskite structure of a perovskite type substance including a plurality of inorganic layers constituting a layered structure and/or a plurality of inorganic chains constituting a chain structure, the method including a step in which only one of S-form chiral molecules and R-form chiral molecules or chiral molecules with a higher abundance proportion of one of S-form chiral molecules and R-form chiral molecules than an abundance proportion of the other of S-form chiral molecules and R-form chiral molecules are incorporated in at least a part of a boundary part between the adjacent inorganic layers and/or between the inorganic chains contained in the perovskite type substance so that the crystal structure of the perovskite type substance is oriented in a predetermined direction.

(19) A thin film according to one aspect of the present invention is a thin film formed of a perovskite type substance and imparted with chirality, the thin film includes a plurality of inorganic layers constituting a layered structure and/or a plurality of inorganic chains constituting a chain structure, and only one of S-form chiral molecules and R-form chiral molecules or chiral molecules with a higher abundance proportion of one of S-form chiral molecules and R-form chiral molecules than an abundance proportion of the other of S-form chiral molecules and R-form chiral molecules which are incorporated in at least a part of a boundary part between the adjacent inorganic layers and/or between the inorganic chains, and the crystal structure of the perovskite type substance is oriented in a predetermined direction.

Advantageous Effects of Invention

According to the present invention, it is possible to provide a thin film that can directly detect circularly polarized light in a wide wavelength range, a method for producing the same, a circularly polarized light detection element including the thin film, a device, and a method.

BRIEF DESCRIPTION OF DRAWINGS

FIGS. 5(a) to 5(c) are graphs showing the results obtained by performing XRD analysis on thin films of Example 1, Example 2, and Comparative Example 3.

FIGS. 10(a) and 10(b) are graphs showing light absorption spectrums and circularly polarized dichroism spectrums of thin films of Comparative Examples 8 and 9.

DESCRIPTION OF EMBODIMENTS (Laminate Structure)

Figure 1:
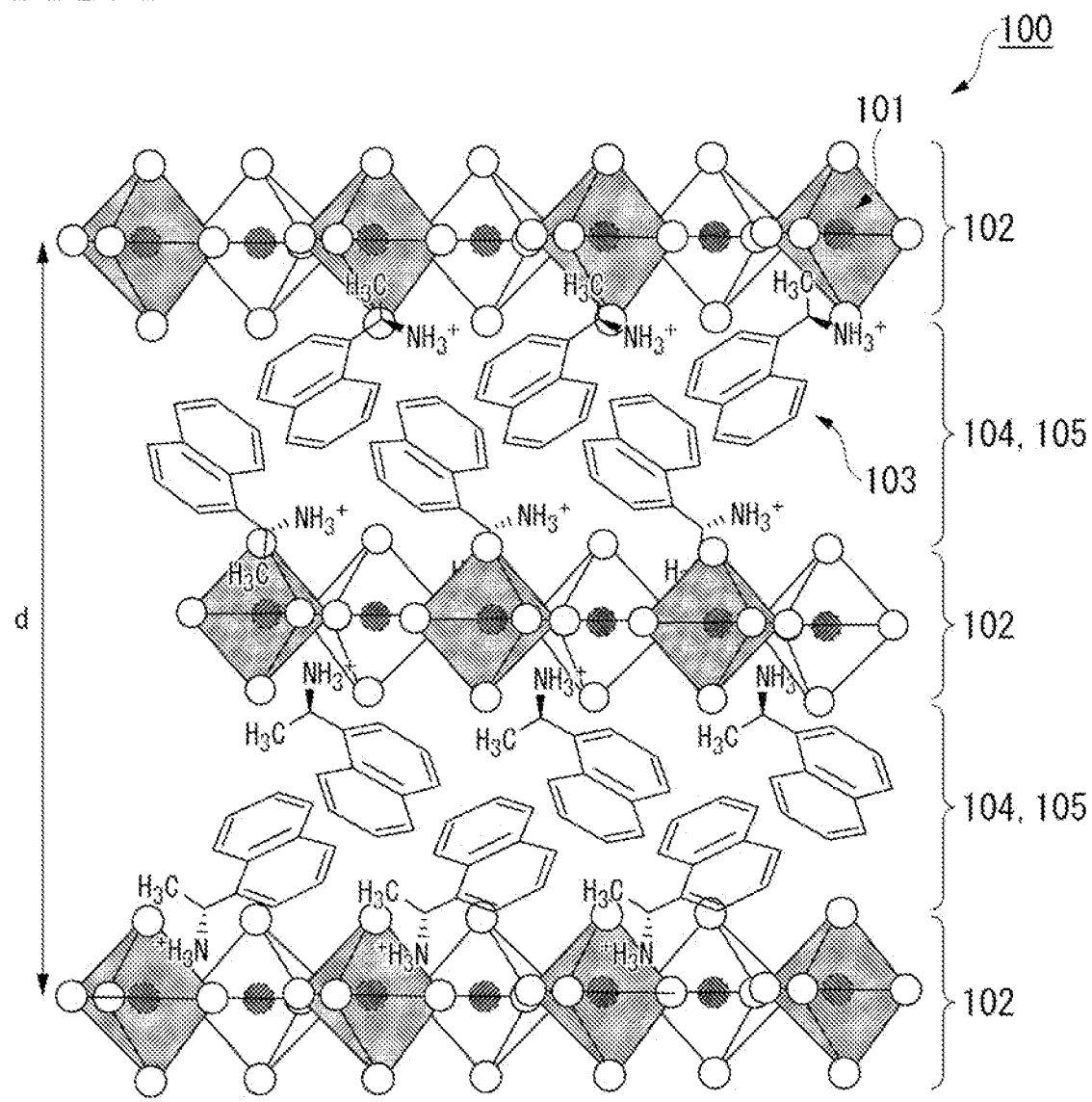
FIG. 1 is a cross-sectional view of a thin film according to one embodiment of the present invention.

Hereinafter, a thin film, a method for producing the same, a circularly polarized light detection element, a device, and a method according to embodiments to which the present invention is applied will be described in detail with reference to the drawings. Here, in the drawings used in the following description, in order to facilitate understanding of features, featured parts are enlarged for convenience of illustration in some cases, and dimensional ratios of components are not necessarily the same as actual ones. In addition, materials, sizes, and the like exemplified in the following description are examples, and the present invention is not limited thereto, and can be realized by appropriate modifications thereof without departing from the gist of the invention.

FIG. 1 is a cross-sectional view schematically showing a configuration of a thin film 100 according to one embodiment of the present invention. The thin film 100 is a thin film for detecting circularly polarized light, and is a thin film formed of a perovskite type substance and imparted with chirality. The thin film 100 is mainly formed of a perovskite type substance 101 and includes a plurality of inorganic layers 102 constituting a layered structure, and chiral molecules 103. Here, in FIG. 1, an amino group has been exemplified as the functional group of the chiral molecules 103, but the present invention is not limited to an amino group.

Each inorganic layer 102 is in the form of a sheet having a thickness of about 1 nm, and constitutes a part of a compound $A_2BX_4$ composed of three types of ions A, B, and X, and is composed of a plurality of perovskite type substances forming a polycrystal structure. The crystal structure of the perovskite type substance has a crystal texture and is oriented in a predetermined direction. Specifically, the ions B and the ions X form a plurality of units $(BX_6)^{4-}$ having an octahedron structure, and octahedron structures of adjacent units share one vertex. The ion B is arranged at the center of the octahedron, and the ion X is arranged at the vertex of the octahedron. In addition, the ion A is arranged at a position circumscribing the octahedron structure of each unit. Here, the ion A is a chiral molecule 103. That is, the perovskite type substance and the chiral molecules 103 constitute a compound $A_2BX_4$ composed of three types of ions A, B, and X.

The inorganic layers 102 are arranged so that octahedron structures share vertices, and the chiral molecules 103 are incorporated between the layers. Thus, this structure is different from the structure in which octahedron structures that share planes are arranged (a structure having an ability to directly detect circularly polarized light in a wavelength range of around 400 nm), and thus a change in the absorption position is caused. As a result, it is possible to impart an ability to directly detect circularly polarized light having a wavelength range extended to 500 nm or more. In addition, it is possible to improve an ability to absorb circularly polarized light when octahedron structures share vertices.

An aromatic compound containing, for example, an ethylammonium ion, as the ion A, may be exemplified. Examples of ions B include lead ions and tin ions. Examples of ions X include halogen ions. Examples of halogen ions include chlorine ions, bromine ions, and iodine ions. Iodine ions are preferable as halogen ions.

The chiral molecules 103 are incorporated in at least a part of a boundary part 104 between adjacent inorganic layers 102 and are bonded and fixed to the perovskite type substance on the surface of the inorganic layer 102. More specifically, the chiral molecules 103 are bonded to the perovskite type substance via functional groups covalently bonded to asymmetric carbon atoms constituting the chiral molecules 103. This functional group is a substituent that can have a charge, and the substituent and the perovskite type substance can form a bond via a halogen ion. As the functional group, an amino group is preferable. When the amino group ($NH_3^+$) is bonded to, for example, $I^-$ of $(PbI_6)^{4-}$, the chirality occurs in the inorganic layer composed of $(PbI_6)^{4-}$, and an ability to absorb circularly polarized light is newly exhibited. The chiral molecule 103 has one or more aromatic rings, and preferably has two or more aromatic rings. In addition, if the aromatic ring is an aromatic ring having a structure that shares one side of a benzene ring such as that of a naphthalene ring or an anthracene ring, this is preferable because the circularly polarized light absorption intensity increases.

Here, the chiral molecules 103 have an R-form or an S-form. The R-form or S-form chiral molecules 103 strongly absorb either right-handed or left-handed circularly polarized light. Here, four different bonding groups are bonded to asymmetric carbon atoms, one with the lowest atomic number is placed farthest away, and the three remaining bonding groups are arranged clockwise (which is called an R-form) or counterclockwise (which is called an S-form) from the one with the highest atomic number to the one with the lowest atomic number. Examples of R-forms include R-(+)-1-(1-naphthyl)ethylamine hydroiodide represented by the following formula (1). Examples of S-forms include S-(−)-1-(1-naphthyl)ethylamine hydroiodide represented by the following formula (2).

[Chem. 1]

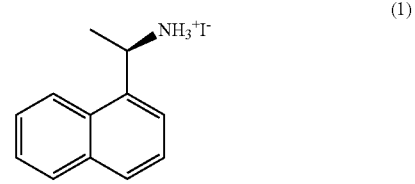

(1)

[Chem. 2]

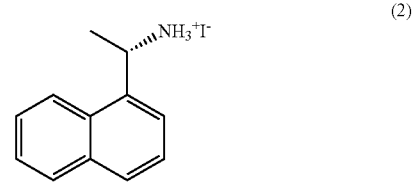

(2)

When 1.2 chiral molecules 103 or more react with one Pb ion molecule of the inorganic layer 102, generally, a layered structure ($A_2BX_4$) is formed, and on the other hand, when 0.75 chiral molecules 103 or less react with one Pb ion molecule of the inorganic layer 102, generally, a chain structure ($ABX_3$) is formed. When more than 0.75 chiral molecules 103 and less than 1.2 chiral molecules 103 react with one Pb molecule of the inorganic layer 102, generally, a structure in which a chain structure and a layered structure are mixed is formed. In the case of the structure in which a chain structure and a layered structure are mixed, the perovskite type substance and chiral molecules constitute compounds $A_2BX_4$ and $ABX_3$ composed of three types of ions A, B, and X. An aromatic compound containing, for example, an ethylammonium ion, as the ion A, may be exemplified. Examples of ions B include lead ions and tin ions. Examples of ions X include halogen ions. Examples of halogen ions include chlorine ions, bromine ions, and iodine ions. Iodine ions are preferable as halogen ions. When the ratio between the chiral molecules 103 and Pb of the inorganic layer 102 is adjusted, it is possible to adjust an ability to absorb circularly polarized light.

FIG. 1 illustrates a case in which the chiral molecules 103 form an organic layer 105 at the boundary part 104, and the inorganic layer 102 and the organic layer 105 are alternately laminated. The number of inorganic layers 102 to be laminated is not limited, but when the thin film 100 is used for a circularly polarized light detection element or the like, the thickness of the thin film 100 is preferably about 100 to 500 nm so that a current easily flows in the thickness direction D. In addition, in order to protect the chiral molecules 103, it is preferable that the uppermost layer and the lowermost layer be laminated to form the inorganic layer 102.

In order to allow the perovskite type substance to absorb emitted light, the surface roughness Ra (arithmetic average roughness) of each thin film 100 is preferably 1 nm or more and 30 nm or less so that the emitted light is efficiently transmitted. If the arithmetic average roughness Ra of the thin film 100 is 30 nm or less, it is possible to minimize leakage of a circularly polarized light detection element 110. The arithmetic average roughness Ra can be measured, for example, using an atomic force microscope (AFM). When measurement is performed using an atomic force microscope, for example, an atomic force microscope (commercially available from Shimadzu Corporation) is used, and the arithmetic average roughness Ra can be obtained from an observation image obtained by performing measurement by setting a scan range and a scan mode to appropriate values (specifically for example, scan mode:dynamic mode).

In addition, since it is necessary for the perovskite type substance to efficiently absorb emitted light, the absorption intensity per unit thickness of the thin film 100 is desirably 50,000 cm$^{-1}$ or more and 500,000 cm$^{-1}$ or less. Here, the absorption intensity per unit thickness is the value of the absorption intensity per unit thickness of the peak wavelength of the peak having the highest absorption intensity. The absorption intensity of the thin film 100 is measured by a transmission method.

Figure 3:
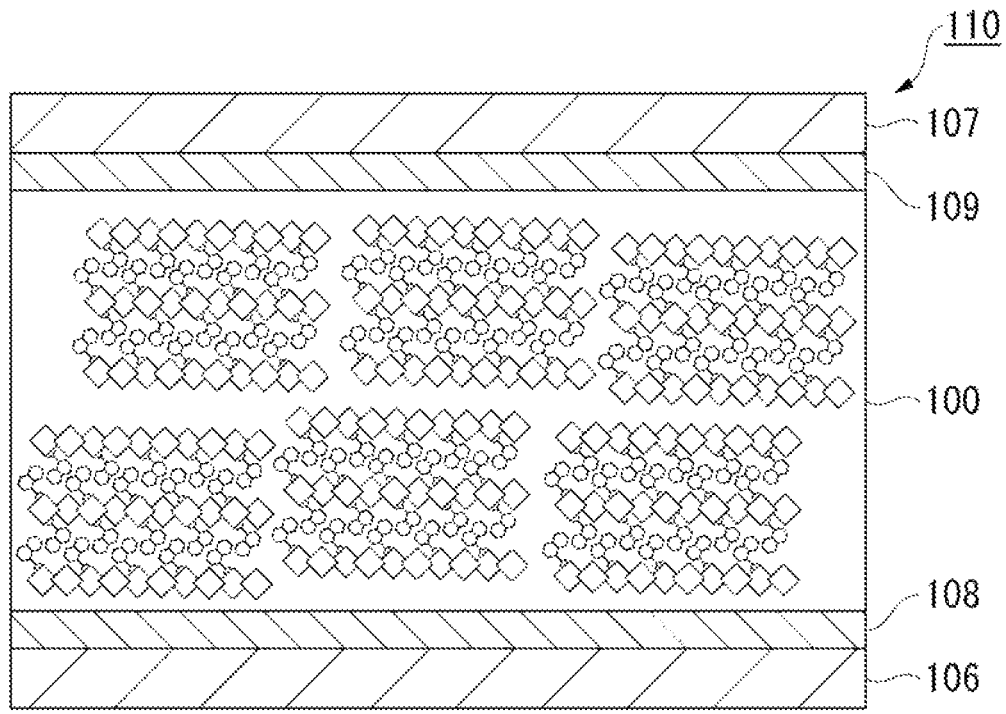
FIG. 3 is a cross-sectional view of a circularly polarized light detection element according to one embodiment of the present invention.

FIG. 3 is a cross-sectional view of the circularly polarized light detection element 110 including the thin film 100. The circularly polarized light detection element 110 is mainly formed by laminating a negative electrode layer 106, the thin film 100, and a positive electrode layer 107 in that order. In order to allow the perovskite type substance in the thin film 100 to absorb light (circularly polarized light), at least one of the negative electrode layer 106 and the positive electrode layer 107 has light transmitting properties. The negative electrode layer 106 is adhered to one side of the thin film 100 in the thickness direction via, for example, a negative electrode-side adhesive layer 108 (electron transport layer) formed of $SnO_2$, $TiO_2$ or the like. The positive electrode layer 107 is adhered to the other side of the thin film 100 in the thickness direction via, for example, a positive electrode-side adhesive layer 109 (hole transport layer) formed of BCP (Bathocuproine (registered trademark)), spiro-MeOTAD, TPD or the like. When the negative electrode layer 106 has light transmitting properties, the negative electrode-side adhesive layer 108 also has light transmitting properties. In addition, when the positive electrode layer 107 has light transmitting properties, the positive electrode-side adhesive layer 109 also has light transmitting properties.

In the circularly polarized light detection element 110, since the inorganic layer 102 constituting the thin film 100 has a polycrystal structure, the thin film 100 has large light absorption (absorption intensity at a wavelength of 488 nm: about 50,000 cm$^{-1}$ or more) and high conductivity (carrier diffusion length, about 1 µm or more). Accordingly, when light emitted to the thin film 100 is circularly polarized light or contains circularly polarized light, a current caused by the absorbed circularly polarized light can be detected. Here, when only R-form or S-form chiral molecules are used, an R- or S-arranged chiral structure can be induced in in the perovskite structure, right-handed circularly polarized light or left-handed circularly polarized light is selectively absorbed, and a current thereof can be detected. In addition, even if the abundance proportion of one of the R-form and the S-form is higher than the abundance proportion of the other of the R-form and the S-form, an R- or S-arranged chiral structure can be induced in in the perovskite structure, right-handed circularly polarized light or left-handed circularly polarized light is selectively absorbed, and a current thereof can be detected (Method for Producing Layered Structure)

When the proportions of the precursor of the perovskite type substance, the chiral molecule, and the organic halide are adjusted, it is possible to control the shape of the perovskite type substance. For example, when a layered structure is formed, the thin film 100 can be mainly produced according to the following procedure. First, the precursor of the perovskite type substance, which is a raw material of the thin film 100, chiral molecules, and organic halides that can be sublimated by heating and react with some of elements constituting the perovskite type substance are dissolved at a ratio of 0.5 mol/L to 2 mol/L, 0.5 mol/L to 2 mol/L, and 1 mol/L or less (preferably 0.4 mol/L to 0.8 mol/L) in a solvent (first step). As the solvent, for example, dimethylformamide (DMF), dimethylsulfoxide (DMSO), γ-butyrolactone or the like can be used. Here, when a layered structure is substantially formed, the ratio is calculated such that 1.2 or more chiral molecules are provided for one Pb ion molecule of the inorganic layer 102, and mixing is performed.

Examples of precursors of perovskite type substances include lead halides. Examples of organic halides include methylammonium halide and formamidinium halide. As the halogen atom contained in the lead halide and organic halide here, for example, any of a bromine atom, a chlorine atom, and an iodine atom may be preferably exemplified.

Next, using a spin coating method, the solution (mixed solution) obtained in the first step is added dropwise onto a separately prepared base substrate and rotated at 1,000 rpm to 5,000 rpm, and thus an untreated coating film is formed on the base substrate (second step). The material of the base substrate is not limited.

Next, the untreated coating film is heated using a heating device, the organic halide contained in the untreated coating film is sublimated (third step), and thus a thin film composed of a polycrystallized inorganic layer and chiral molecules distributed therebetween can be obtained. Here, preferably, the heating temperature is about 70° C. to 120° C., and the heating time is about 15 minutes to 60 minutes.

When the solution obtained in the first step that is not crystallized is subjected to treatments of the second step and the third step, the inorganic layer 102 of the thin film 100 obtained through the third step has a crystal texture and is not random but is a polycrystal that is preferentially oriented in a specific direction.

Using a known film filming method such as vacuum deposition or a sputtering method, the positive electrode layer 107 is formed on one side of the thin film 100 obtained through the third step in the thickness direction, and the negative electrode layer 106 is formed on the other side thereof, and thus it is possible to obtain a circularly polarized light detection element 110 that can output circularly polarized light information as an electrical signal. Here, using a known film filming method such as vacuum deposition, spin coating, or a sputtering method, the positive electrode-side adhesive layer 109 and the negative electrode-side adhesive layer 108 may be formed between the thin film 100 and the positive electrode layer 107, and between the thin film 100 and the negative electrode layer 106 respectively.

As described above, the thin film 100 of the present embodiment is a layered structure in which the plurality of inorganic layers 102 stack, and the chiral molecules 103 having absorbance against circularly polarized light are fixed in a nano space that is interposed between adjacent inorganic layers 102 and spreads two-dimensionally. The chiral molecules 103 induce chirality in the arrangement of the inorganic layers 102 so that the absorption wavelength range of circularly polarized light according to the inorganic layer 102 can be extended to a wide range of 350 to 800 nm.

In addition, since the inorganic layer 102 has a polycrystal structure and has high conductivity, by connecting electrodes to both ends in the thickness direction, when light emitted to the thin film 100 is circularly polarized light or contains circularly polarized light, a current caused by the circularly polarized light absorbed by the inorganic layer 102 can be detected. That is, the inorganic layer 102 formed using only R-arranged chiral molecules or S-arranged chiral molecules can selectively absorb right-handed circularly polarized light or left-handed circularly polarized light, and a current thereof can be detected.

In addition, since the thin film 100 of the present embodiment does not need to use a polarizer or a wavelength plate in order to detect circularly polarized light, a high extinction ratio is obtained. It is possible to directly detect circularly polarized light with high sensitivity and high resolution, which is unable to be directly detected with conventional light detection elements.

Accordingly, the thin film 100 of the present embodiment can be utilized as a circularly polarized light detection element, and various devices such as a polarization camera incorporating the circularly polarized light detection element incorporating the thin film can be realized. When circularly polarized light is directly detected, it is possible to obtain information such as an intensity distribution of double refraction, which cannot be obtained from linearly polarized light.

(Chain Structure)

Figure 2:
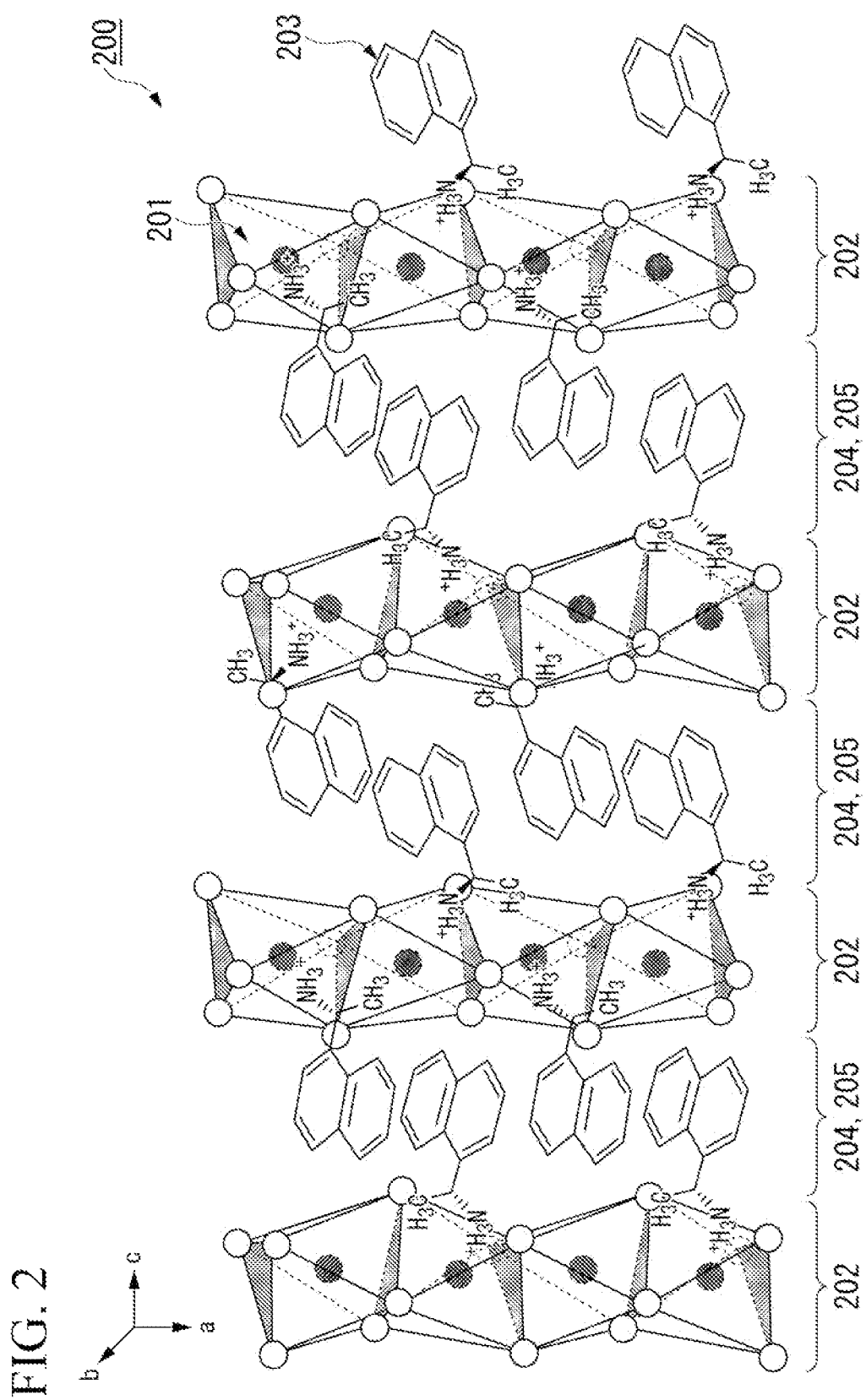
FIG. 2 is a cross-sectional view of a thin film according to another embodiment of the present invention.

Next, a case of a chain structure will be described. FIG. 2 is a cross-sectional view schematically showing a configuration of a thin film 200 according to one embodiment of the present invention. The thin film 200 is a thin film formed of a perovskite type substance and imparted with chirality. The thin film 200 is mainly formed of a perovskite type substance 201 and includes a plurality of inorganic chains 202 constituting a chain structure, and chiral molecules 203. The chain structure is preferable because it can have a larger anisotropy factor than the layered structure. Here, in FIG. 2, an amino group has been exemplified as the functional group of the chiral molecules 203, but the present invention is not limited to an amino group.

Each inorganic chain 202 is a chain structure having a diameter of about 1 nm, and constitutes a part of the compound $ABX_3$ composed of three types of ions A, B, and X, and is composed of a plurality of perovskite type substances forming a polycrystal structure. The crystal structure of the perovskite type substance has a crystal texture, and is oriented in a predetermined direction. Specifically, the ions B and the ions X form a plurality of units $(BX_6)^{4-}$ having an octahedron structure, and octahedron structures of adjacent units share one plane. The ion B is arranged at the center of the octahedron, and the ion X is arranged at the vertex of the octahedron. In addition, the ion A is arranged at a position circumscribing the octahedron structure of each unit. Here, the ion A is a chiral molecule 203. That is, the perovskite type substance and the chiral molecules constitute a compound $ABX_3$ composed of three types of ions A, B, and X.

The inorganic chains 202 are arranged so that octahedron structures share planes, and the chiral molecules 203 surround the inorganic chains 202. Thus, this structure is different from the structure in which octahedron structures that share vertices are arranged (a structure having an ability to directly detect circularly polarized light in a wavelength range of around 500 nm), and thus a change in the absorption position is caused. As a result, it is possible to impart an ability to directly detect circularly polarized light in a wavelength range of around 400 nm. In addition, it is possible to increase an ability to absorb circularly polarized light when octahedron structures share planes.

An aromatic compound containing, for example, an ethylammonium ion, as the ion A, may be exemplified. Examples of ions B include lead ions and tin ions. Examples of ions X include halogen ions. Examples of halogen ions include $F^-$, $Cl^-$, $Br^-$ and $I^-$. $I^-$ is preferable as a halogen ion.

The chiral molecules 203 are incorporated in at least a part of a boundary part 204 between adjacent inorganic chains 202, and are bonded and fixed to the perovskite type substance on the surface of the inorganic chain 202. More specifically, the chiral molecules 203 are bonded to the perovskite type substance via functional groups covalently bonded to asymmetric carbon atoms constituting the chiral molecules 203. This functional group is a substituent that can have a charge, and the substituent and the perovskite type substance can form a bond via a halogen ion. As the functional group, an amino group is preferable. When the amino group ($NH_3^+$) is bonded to, for example, $I^-$ of $(PbI_6)^{4-}$, the chirality occurs in the inorganic chain composed of $(PbI_6)^{4-}$, and an ability to absorb circularly polarized light is newly exhibited. The chiral molecule 203 has one or more aromatic rings, and preferably has two or more aromatic rings. In addition, if the aromatic ring is an aromatic ring having a structure that shares one side of a benzene ring such as that of a naphthalene ring or an anthracene ring, this is preferable because the circularly polarized light absorption intensity increases.

Here, the chiral molecules 203 have an R-form or an S-form. The R-form or S-form chiral molecules 203 strongly absorb either right-handed or left-handed circularly polarized light. Examples of R-forms include R-(+)-1-(1-naphthyl) ethylamine hydroiodide represented by Formula (1). Examples of S-forms include S-(−)-1-(1-naphthyl) ethylamine hydroiodide represented by Formula (2).

FIG. 2 illustrates a case in which the chiral molecules 203 form an organic layer 205 at the boundary part 204, and the organic layer 205 covers the surroundings of the inorganic chain 202. The inorganic chain 202 may be connected to another the inorganic chain 202 in the b-axis direction via the organic layer 205. In addition, in the c-axis direction, aromatic rings of organic molecules bonded to inorganic chains are stacked. The number of inorganic chains 202 to be connected is not limited. When the thin film 200 is used for a circularly polarized light detection element or the like, the thickness of the thin film 200 is preferably about 100 to 500 nm so that a current easily flows in thickness direction D.

In order to allow the perovskite type substance to absorb emitted light, the surface roughness Ra (arithmetic average roughness) of each thin film 200 is preferably 1 nm or more and 30 nm or less so that emitted light is efficiently transmitted. In addition, if the arithmetic average roughness Ra of the thin film 200 is 30 nm or less, it is possible to minimize leakage of the circularly polarized light detection element 220. The arithmetic average roughness Ra can be measured, for example, using an atomic force microscope (AFM). When measurement is performed using an atomic force microscope, for example, an atomic force microscope (commercially available from Shimadzu Corporation) is used, and the arithmetic average roughness Ra can be obtained from an observation image obtained by performing measurement by setting a scan range and a scan mode to appropriate values (specifically for example, scan mode: dynamic mode).

In addition, since it is necessary for the perovskite type substance to efficiently absorb emitted light, the absorption intensity per unit thickness of the thin film 200 is desirably 50,000 $cm^{-1}$ or more and 500,000 $cm^{-1}$ or less. Here, the absorption intensity per unit thickness is the value of the peak wavelength of the peak having the highest absorption intensity. The absorption intensity of the thin film 200 is measured by a transmission method.

Figure 4:
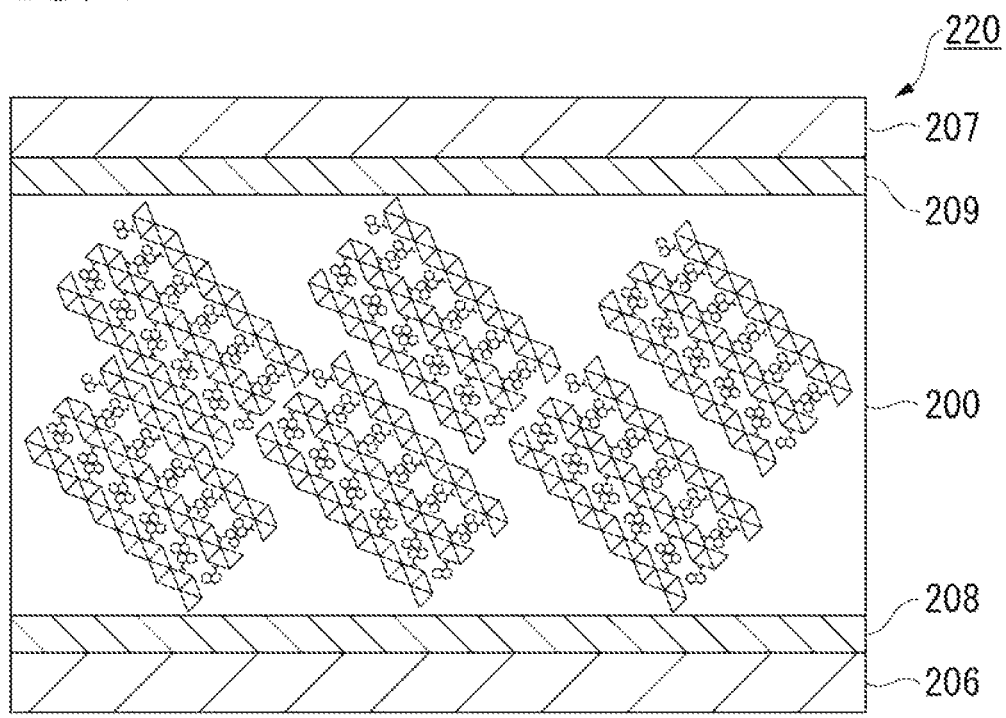
FIG. 4 is a cross-sectional view of a circularly polarized light detection element according to another embodiment of the present invention.

FIG. 4 is a cross-sectional view of the circularly polarized light detection element 220 including the thin film 200. The circularly polarized light detection element 220 is mainly formed by laminating a negative electrode layer 206, the thin film 200, and a positive electrode layer 207 in that order. In order to allow the perovskite type substance in the thin film 200 to absorb light (circularly polarized light), at least one of the negative electrode layer 206 and the positive electrode layer 207 has light transmitting properties. The negative electrode layer 206 is adhered to one side of the thin film 200 in the thickness direction via, for example, a negative electrode-side adhesive layer 208 formed of $SnO_2$, $TiO_2$ or the like (electron transport layer). The positive electrode layer 207 is adhered to the other side of the thin film 200 in the thickness direction via, for example, a positive electrode-side adhesive layer 209 (hole transport layer) formed of BCP (Bathocuproine (registered trademark)), spiro-MeOTAD, TPD or the like. When the negative electrode layer 206 has light transmitting properties, the negative electrode-side adhesive layer 208 also has light transmitting properties. In addition, when the positive electrode layer 207 has light transmitting properties, the positive electrode-side adhesive layer 209 also has light transmitting properties.

In the circularly polarized light detection element 220, since the inorganic chain 202 constituting the thin film 200 has a polycrystal structure, the thin film 200 has large light absorption (absorption intensity at a wavelength of 375 nm: about 50,000 $cm^{-1}$ or more) and has conductivity (carrier diffusion length, about 1 μm or more). Accordingly, when light emitted to the thin film 200 is circularly polarized light or contains circularly polarized light, a current caused by the absorbed circularly polarized light can be detected. Here, when only R-form or S-form chiral molecules are used, an R- or S-arranged chiral structure can be induced in in the perovskite structure, right-handed circularly polarized light or left-handed circularly polarized light is selectively absorbed, and a current thereof can be detected (Method for Producing Chain Structure)

When the proportions of the precursor of the perovskite type substance, the chiral molecule, and the organic halide are adjusted, it is possible to control the shape of the perovskite type substance. For example, when a chain structure is formed, the thin film 200 can be mainly produced according to the following procedure. First, the precursor of the perovskite type substance, which is a raw material of the thin film 200, chiral molecules, and organic halides that can be sublimated by heating and react with some of elements constituting the perovskite type substance are dissolved at a ratio of 0.5 mol/L to 2 mol/L, 0.5 mol/L to 2 mol/L, and 1 mol/L or less (preferably 0.4 mol/L to 0.8 mol/L) in a (first step). As the solvent, for example, dimethylformamide (DMF), dimethylsulfoxide (DMSO), γ-butyrolactone or the like can be used. Here, when a plurality of inorganic chains substantially form a chain structure, the ratio is calculated such that 0.75 chiral molecules or less are provided for one Pb ion molecule of the inorganic chain 202, and mixing is performed.

Examples of precursors of perovskite type substances include lead halides. Examples of organic halides include methylammonium halide and formamidinium halide. As the halogen atom contained in the lead halide and organic halide here, for example, any of a bromine atom, a chlorine atom, and an iodine atom may be preferably exemplified.

Next, using a spin coating method, the solution (mixed solution) obtained in the first step is added dropwise onto a separately prepared base substrate and rotated at 1,000 rpm to 5,000 rpm, and thus an untreated coating film is formed on the base substrate (second step). The material of the base substrate is not limited.

Next, the untreated coating film is heated using a heating device, the organic halide contained in the untreated coating film is sublimated (third step), and thus a thin film composed of a polycrystallized inorganic layer and chiral molecules distributed therebetween can be obtained. Here, preferably, the heating temperature is about 70° C. to 120° C., and the heating time is about 15 minutes to 60 minutes.

When the solution obtained in the first step that is not crystallized is subjected to treatments of the second step and the third step, the inorganic chain 202 of the thin film 200 obtained through the third step has a crystal texture and is not random but is a polycrystal that is preferentially oriented in a specific direction.

Using a known film filming method such as vacuum deposition or a sputtering method, the positive electrode layer 207 is formed on one side of the thin film 200 obtained through the third step in the thickness direction, and the negative electrode layer 206 is formed on the other side thereof, and thus it is possible to obtain the circularly polarized light detection element 220 that can output circularly polarized light information as an electrical signal. Here, using a known film filming method such as vacuum deposition, spin coating, or a sputtering method, the positive electrode-side adhesive layer 209 and the negative electrode-side adhesive layer 208 may be formed between the thin film 200 and the positive electrode layer 207, and between the thin film 200 and the negative electrode layer 206 respectively.

As described above, the thin film 200 of the present embodiment is a chain structure in which the inorganic chains 202 are arranged and the chiral molecules 203 having absorbance against circularly polarized light are fixed in a nano space that is interposed between the adjacent inorganic chains 202 and spreads one-dimensionally. The chiral molecules 203 induce chirality in the arrangement of the inorganic chains 202 so that the absorption wavelength range of circularly polarized light according to the inorganic chain 202 can be extended to a wide range of 350 nm to 800 nm.

In addition, since the inorganic chain 202 has a polycrystal structure and has high conductivity, by connecting electrodes to both ends in the thickness direction, when light emitted to the thin film 200 is circularly polarized light or contains circularly polarized light, a current caused by the circularly polarized light absorbed by the inorganic chain 202 can be detected. That is, the inorganic chain 202 formed using only R-arranged chiral molecules or S-arranged chiral molecules can selectively absorb right-handed circularly polarized light or left-handed circularly polarized light, and a current thereof can be detected. In addition, even if the abundance proportion of one of the R-form and the S-form is higher than the abundance proportion of the other of the R-form and the S-form, an R- or S-arranged chiral structure can be induced in in the perovskite structure, right-handed circularly polarized light or left-handed circularly polarized light is selectively absorbed, and a current thereof can be detected In addition, the thin film 200 of the present embodiment does not need to use a polarizer or a wavelength plate in order to detect circularly polarized light, a high extinction ratio is obtained. It is possible to directly detect circularly polarized light with high sensitivity and high resolution, which is unable to be directly detected with conventional light detection elements.

Accordingly, the thin film 200 of the present embodiment can be utilized as a circularly polarized light detection element, and various devices such as a polarization camera incorporating the circularly polarized light detection element incorporating the thin film can be realized. When circularly polarized light is directly detected, it is possible to obtain information such as an intensity distribution of double refraction, which cannot be obtained from linearly polarized light.

As described above, according to the method in which only one of S-form chiral molecules 103, 203 and R-form chiral molecules 103, 203 or the chiral molecules 103, 203 with a higher abundance proportion of one of S-form chiral molecules and R-form chiral molecules than an abundance proportion of the other of S-form chiral molecules and R-form chiral molecules are incorporated in at least a part of a boundary part between the adjacent inorganic layers 102 and/or between the inorganic chains 202 contained in the perovskite type substance so that the crystal structure of the perovskite type substance is oriented in a predetermined direction, it is possible to induce the R- or S-arranged chiral structure in the perovskite structure of the perovskite type substance including the plurality of inorganic layers 102 constituting the layered structure and/or the plurality of inorganic chains 202 constituting the chain structure, and it is possible to directly detect circularly polarized light.

EXAMPLES

Hereinafter, the effects of the present invention will become more apparent from examples. However, the present invention is not limited to the following examples, but can be appropriately changed and implemented within ranges without changing the gist of the invention.

Example 1

The method for producing a thin film according to the above embodiment was performed according to the following procedure to prepare a thin film. 1 g of R-(+)-1-(1-naphthyl) ethylamine (R-1-NEA) and 500 μL of hydrogen iodide (HI) were mixed, and the obtained mixture was stirred at 0° C. for 2 hours to obtain 2.8 g of R-(+)-1-(1-naphthyl) ethylamine hydroiodide ((R-1-NEA)I). Subse-
quently, in 500 μL of dimethylformamide (DMF) as a solvent, 230 mg of lead iodide ($PbI_2$), 299 mg of ((R-1-NEA)I) and 60 mg of methylamine hydroiodide (MAI) were mixed, and the obtained mixture was stirred at 70° C. for 1 hour to prepare a solution containing a raw material of the thin film. The prepared solution was applied onto a separately prepared base substrate and an untreated coating film was formed by a spin coating method (1,000 rpm, 10 s/5,000 rpm, 60 s), the formed untreated coating film was heated at 100° C. for 30 minutes, and thereby a thin film of (R-1-NEA)$_2$PbI$_4$ was obtained.

Example 2

1 g of S-(−)-1-(1-naphthyl) ethylamine (S-1-NEA) and 500 μL of hydrogen iodide (HI) were mixed, and the obtained mixture was stirred at 0° C. for 2 hours to obtain 2.9 g of S-(+)-1-(1-naphthyl) ethylamine hydroiodide ((S-1-NEA)I). Subsequently, in 500 μL of dimethylformamide (DMF) as a solvent, 230 mg of lead iodide ($PbI_2$), 299 mg of ((S-1-NEA)I) and 60 mg of methylamine hydroiodide (MAI) were mixed, and the obtained mixture was stirred at 70° C. for 1 hour to prepare a solution containing a raw material of the thin film. Subsequently, in the same procedure as in Example 1, spin coating was performed, and heating was then performed (100° C., 30 minutes), and thereby a thin film of (S-1-NEA)$_2$PbI$_4$ was obtained.

Comparative Example 3

1 g of racemate DL-1-(1-naphthyl) ethylamine (rac-1-NEA) and 500 μL of hydrogen iodide (HI) were mixed, the mixture was stirred at 0° C. for 2 hours, and thereby 2.8 g of DL-1-(1-naphthyl) ethylamine hydroiodide ((rac-1-NEA) I) was obtained. Subsequently, in 500 μL of dimethylformamide (DMF) as a solvent, 230 mg of lead iodide ($PbI_2$), 299 mg of ((rac-1-NEA)I) and 60 mg of methylamine hydroiodide (MAI) were mixed, and the obtained mixture was stirred at 70° C. for 1 hour to prepare a solution containing a raw material of the thin film. Subsequently, in the same procedure as in Example 1, spin coating was performed, and heating was then performed (100° C., 30 minutes), and thereby a thin film of (rac-NEA)$_2$PbI$_4$ was obtained.

Example 4

The method for producing a thin film according to the above embodiment was performed according to the following procedure to prepare a thin film. 1 g of R-(+)-1-(1-naphthyl) ethylamine (R-1-NEA) and 500 μL of hydrogen iodide (HI) were mixed, and the obtained mixture was stirred at 0° C. for 2 hours to obtain 2.8 g of R-(+)-1-(1-naphthyl) ethylamine hydroiodide ((R-1-NEA)I). Subsequently, in 500 μL of dimethylformamide (DMF) as a solvent, 230 mg of lead iodide ($PbI_2$), 112 mg of ((R-1-NEA)I) and 60 mg of methylamine hydrogen iodide (MAI) were mixed, and the obtained mixture was stirred at 70° C. for 1 hour to prepare a solution containing a raw material of the thin film. The prepared solution was applied onto a separately prepared base substrate, and an untreated coating film was formed by a spin coating method. The formed untreated coating film was heated at 100° C. for 30 minutes, and thereby a thin film of (R-1-NEA)PbI$_3$ was obtained.

Example 5

1 g of S-(−)-1-(1-naphthyl) ethylamine (S-1-NEA) and 500 μL of hydrogen iodide (HI) were mixed, and the obtained mixture was stirred at 0° C. for 2 hours to obtain 2.9 g of S-(+)-1-(1-naphthyl) ethylamine hydroiodide ((S-1-NEA)I). Subsequently, in 500 µL of dimethylformamide (DMF) as a solvent, 230 mg of lead iodide (PbI$_2$), 112 mg of ((S-1-NEA)I) and 60 mg of methylamine hydroiodide (MAI) were mixed, and the obtained mixture was stirred at 70° C. for 1 hour to prepare a solution containing a raw material of the thin film. Subsequently, in the same procedure as in Example 1, spin coating was performed, and heating was then performed (100° C., 30 minutes), and thereby a thin film of (S-1-NEA)PbI$_3$ was obtained.

Comparative Example 6

1 g of racemate DL-1-(1-naphthyl) ethylamine (rac-1-NEA) and 500 µL of hydrogen iodide (HI) were mixed, the obtained mixture was stirred at 0° C. for 2 hours, and thereby 2.8 g of DL-1-(1-naphthyl) ethylamine hydroiodide ((rac-1-NEA)I) was obtained. Subsequently, in 500 µL of dimethylformamide (DMF) as a solvent, 230 mg of lead iodide (PbI$_2$), 112 mg of ((rac-1-NEA)I) and 60 mg of methylamine hydroiodide (MAI) were mixed, and the obtained mixture was stirred at 70° C. for 1 hour to prepare a solution containing a raw material of the thin film. Subsequently, in the same procedure as in Example 1, spin coating was performed, and heating was then performed (100° C., 30 minutes), and thereby a thin film of (rac-1-NEA)PbI$_3$ was obtained.

Comparative Example 7

A thin film was prepared in the same method as in Example 1 except that methylamine hydriodic acid was not used.

Comparative Example 8

A thin film was prepared in the same method as in Example 4 except that methylamine hydriodic acid was not used.

Comparative Example 9

A thin film was prepared in the same method as in Example 5 except that methylamine hydriodic acid was not used.

(Measurement of Surface Roughness)

For Examples 1, 2, 4 and 5, and Comparative Examples 3, and 6 to 9, atomic force microscope measurement was performed. SPM-9700 (cantilever for Si dynamic mode, commercially available from Shimadzu Corporation) was used as the atomic force microscope, and measurement was performed in a dynamic mode. The arithmetic average roughness Ra was obtained from the obtained observation image.

(XRD Measurement)

For Examples 1, 2, 4 and 5, and Comparative Examples 3, and 6 to 9, D8 DISCOVER (commercially available from BrukerAXS) was used as an X-ray diffraction measurement device, and the X-ray diffraction pattern of each thin film was measured by an X-ray diffraction (XRD) method at room temperature. In the measurement, the radiation source was CuKα, an X-ray collimator (0.3 mmφ) was used, and a two-dimensional detector (VANTEC-500) was used as a detector. The tube voltage and the tube current during measurement were 40 kV and 40 mA, respectively. The measurement conditions were 1° for ω, 10° for 2θ, and 300 seconds for the accumulation time.

(Measurement of Light Absorption Spectrum)

For Examples 1, 2, 4 and 5, and Comparative Examples 3, and 6 to 9, measurement was performed using an ultraviolet and visible spectrophotometer (J-1500 commercially available from JASCO Corporation), and the light absorption spectrum of each thin film was obtained.

(Measurement of Circularly Polarized Dichroism Spectrum)

For Examples 1, 2, 4 and 5, and Comparative Examples 3, and 6 to 9, measurement was performed using a circular dichroism spectrometer (J-1500 commercially available from JASCO Corporation), and the circularly polarized dichroism spectrum of each thin film was obtained.

(Measurement of Photocurrent and Dark Current Characteristics)

A thin film was formed on a substrate (glass with highly durable transparent conductive film commercially available from Geomatec Co., Ltd.) having a negative electrode layer formed by a sputtering or vacuum deposition method under the same conditions as in Examples 1 and 4. Then, a positive electrode layer (silver, a thickness of 80 to 100 nm) was formed on the opposite side in the thickness direction by a sputtering or vacuum deposition method. A voltage was applied between the positive electrode layer and the negative electrode layer, and a current flowing when light was emitted to the thin film (right-handed circularly polarized light, left-handed circularly polarized light) was measured with a SourceMeter 2450 (commercially available from Keithley). For light emission, light obtained by separating light of a xenon light source of Max350 (commercially available from Asahi Spectra Co., Ltd.) with a monochromator (CMS-100) was used. The emission intensity was 1 mW/cm$^2$. The emitted light was formed into circularly polarized light using a linear polarizer and a ¼ wavelength plate (commercially available from Thorlabs Japan Inc.).

(Measurement of On-Off Characteristics)

Light (right-handed circularly polarized light, left-handed circularly polarized light) was emitted to the sample on which the positive electrode layer and the negative electrode layer were formed at certain intervals, and on-off characteristics were measured.

FIGS. 5(a) to 5(c) show the results of XRD analysis of the thin films obtained in Example 1, Example 2, and Comparative Example 3. The horizontal axis in FIGS. 5(a) to 5(c) represents diffraction angle, and the vertical axis in FIGS. 5(a) to 5(c) represents diffraction intensity. FIG. 5(a) shows the measurement results of the thin film of Example 1, FIG. 5(b) shows the results of the thin film of Example 2, and FIG. 5(c) shows the results of the thin film of Comparative Example 3. All of the thin films of Example 1, Example 2, and Comparative Example 3 showed periodic diffraction patterns corresponding to the (002), (004), (006), (008), and (0010) planes at 5.83, 11.7, 17.6, 23.5, and 29.5°. The space group of this thin film crystal had an interplanar interval of d=30 Å due to the Bragg's reflection condition (2d sin θ=nλ). That is, it was found that layer compounds were formed at intervals of 30 Å when chiral molecules were inserted between inorganic layers formed of a perovskite type substance.

Figures 6A, 6B, 6C:
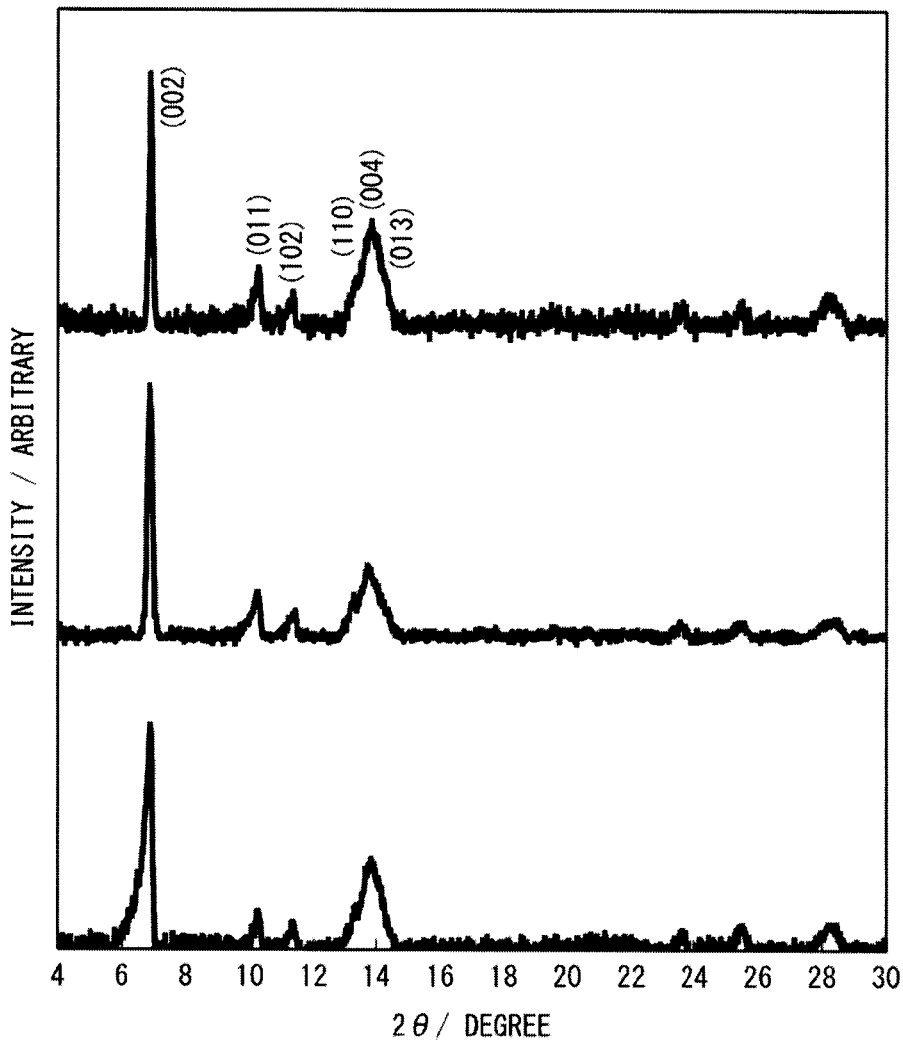
FIGS. 6(a) to 6(c) are graphs showing the results obtained by performing XRD analysis on thin films of Example 4, Example 5, and Comparative Example 6.

FIGS. 6(a) to 6(c) show the results of XRD measurement of the thin films obtained in Example 4, Example 5, and Comparative Example 6. The horizontal axis in FIGS. 6(a) to 6(c) represents diffraction angle, and the vertical axis in FIGS. 6(a) to 6(c) represents diffraction intensity. FIG. 6(a) shows the measurement results of the thin film of Example 4, FIG. 6(b) shows the results of the thin film of Example 5, and FIG. 6(c) shows the results of the thin film of Comparative Example 6. All of the thin films of Example 4, Example 5, and Comparative Example 6 showed diffraction patterns corresponding to the (002), (011), (102), (110), (004), and (013) planes at 6.84, 10.2, 11.3, 13.2, 13.7, and 24.3°, and showed a crystal structure belonging to the chiral space group ($P2_12_12_1$). Within the crystal, adjacent octahedron structures $(PbI_6)^{4-}$ shared one plane to form a one-dimensional chain. It was found that a spiral structure was induced in the chain by surrounding this one-dimensional chain with 1-NEA.

Figure 7A:
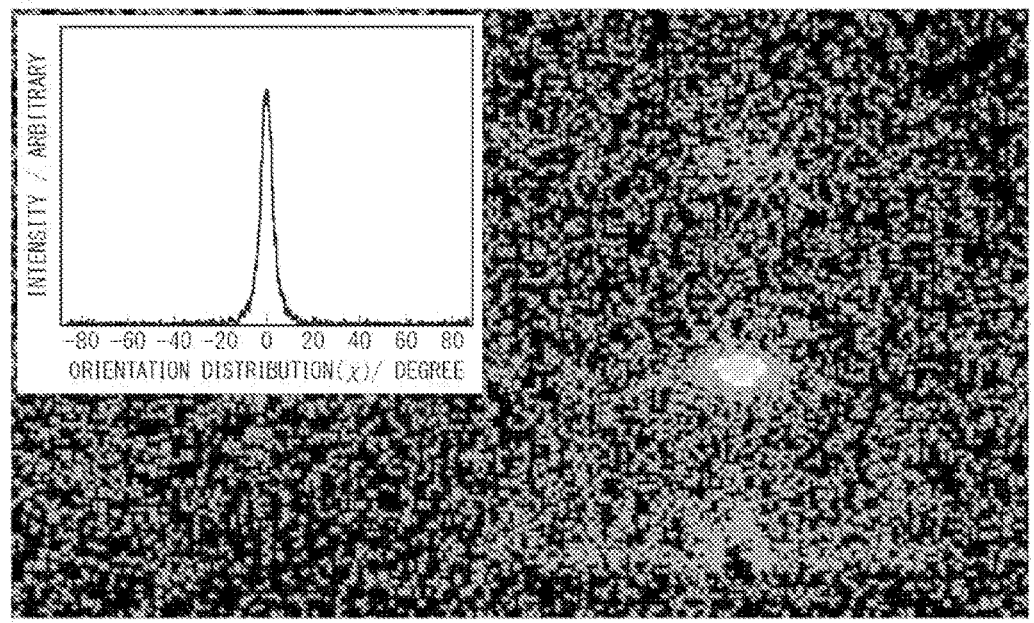
FIGS. 7(a) and 7(b) are graphs showing the results obtained by performing XRD analysis on thin films of Examples 1 and 4 using a two-dimensional detector.
Figure 7B:
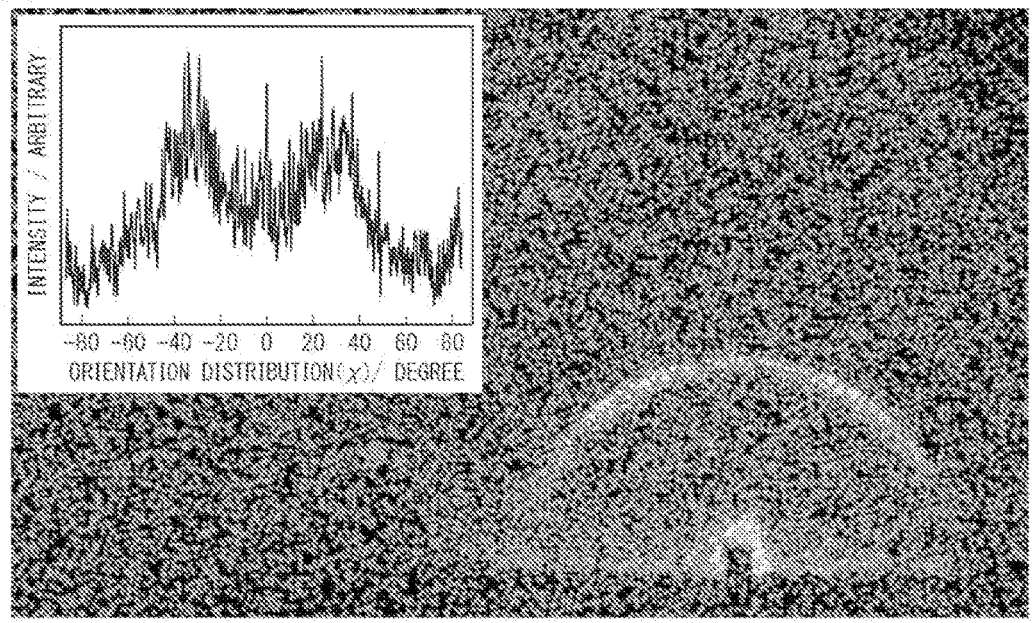

FIGS. 7(a) and 7(b) show the results of XRD measurement of the thin film of Example 1 and the thin film of Example 4 using a two-dimensional detector. The drawings inserted in FIGS. 7(a) and 7(b) are diagrams showing the orientation distribution of the (002) plane. It was found that, in the thin film of Example 1, the (002) plane was strongly oriented in the out-of-plane direction (FIG. 7(a)). That is, it means that the inorganic layer formed of perovskite was laminated in parallel with the substrate. The thin film of Example 4 showed a peak of the (002) plane at a position just intermediate between the out-of-plane direction and the in-plane direction (FIG. 7(b)). This means that the chain formed of perovskite was diagonally oriented.

Figure 8A:
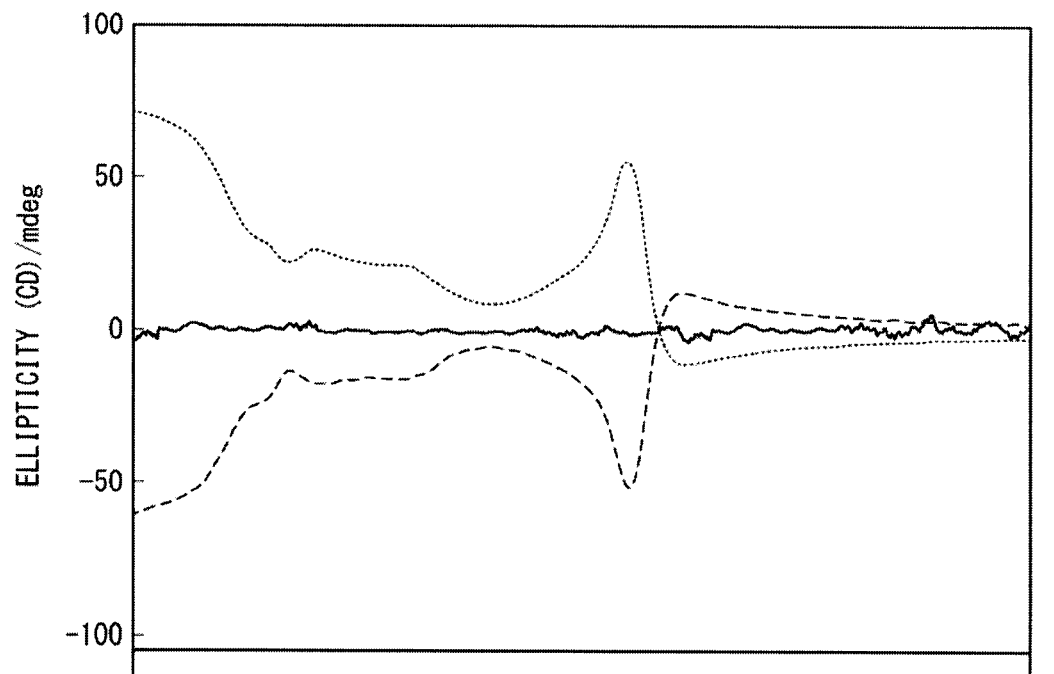
FIGS. 8(a) and 8(b) are graphs showing light absorption spectrums and circularly polarized dichroism spectrums of thin films of Example 1, Example 2, and Comparative Example 3.

FIG. 8(a) shows the measurement results of the circularly polarized dichroism spectrum (CD spectrum) of the thin films of Example 1, Example 2, and Comparative Example 3. The horizontal axis in FIG. 8(a) represents wavelength, and the vertical axis in FIG. 8(a) represents CD signal strength (CD[mdeg]=32980×Δ absorbance (difference in absorption intensities between left-handed circularly polarized light and right-handed circularly polarized light)). The broken line in FIG. 8(a) indicates the CD spectrum of Example 1, the dotted line indicates the CD spectrum of Example 2, and the solid line indicates the CD spectrum of Comparative Example 3. The thin film of Example 1 showed a CD signal of −56 mdeg at 488 nm. That is, the thin film of Example 1 exhibited stronger absorption against right-handed circularly polarized light than left-handed circularly polarized light. The thin film of Example 2 showed a CD signal in the opposite direction and exhibited stronger absorption against left-handed circularly polarized light. Since the racemic thin film of Comparative Example 3 did not show a CD signal, circularly polarized light could not be discriminated. The anisotropy factor ($g_{CD}$) for discriminating circularly polarized light of the thin film having a two-dimensional structure was 0.003. This $g_{CD}$ value was higher than a gCD of a general organic chiral molecule by one order or more.

Figure 8B:
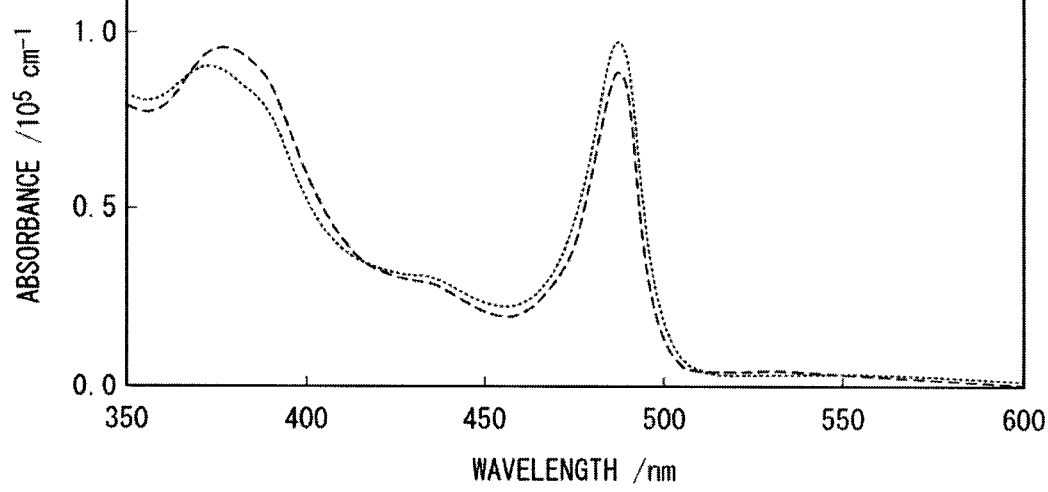

FIG. 8(b) shows the light absorption spectrum measurement results of the thin films of Example 1, Example 2, and Comparative Example 3. The horizontal axis in FIG. 8(b) represents wavelength, and the vertical axis in FIG. 8(b) represents absorbance. The broken line in FIG. 8(b) indicates the light absorption spectrum of Example 1, and the dotted line indicates the light absorption spectrum of Example 2. The thin films of Examples 1 and 2 had a peak at 488 nm. The absorption intensity per unit thickness of the thin film of Example 1 was 89,286 $cm^{-1}$. The absorption intensity per unit thickness of the thin film of Example 2 was 96,7517 $cm^{-1}$. Here, the light absorption spectrum of Comparative Example 3 was the same as those of Examples 1 and 2.

Figure 9A:
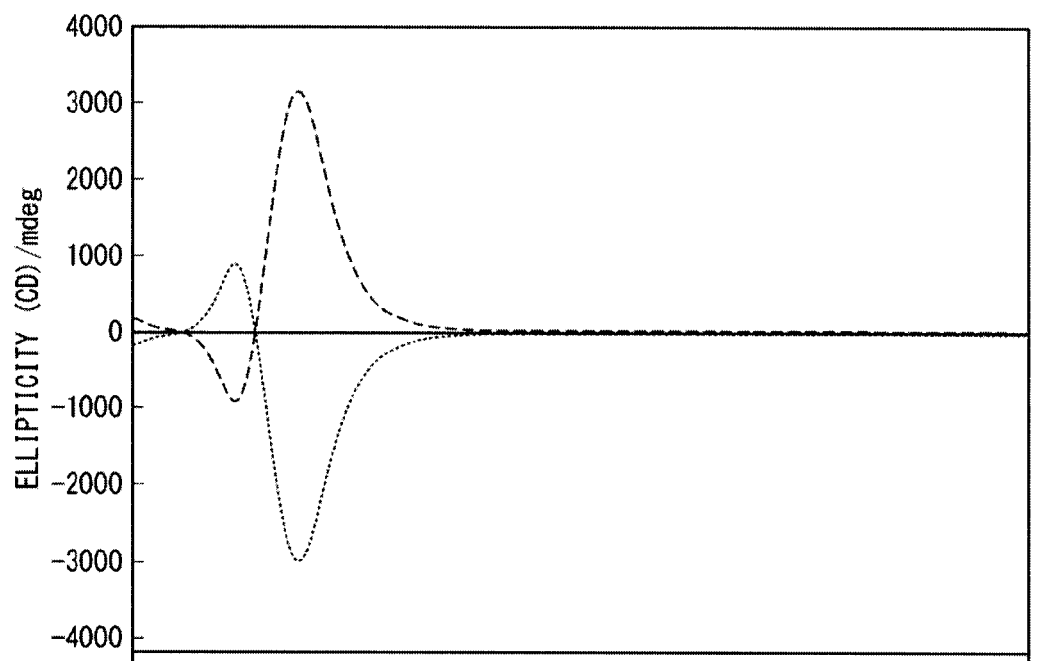
FIGS. 9(a) and 9(b) are graphs showing light absorption spectrums and circularly polarized dichroism spectrums of thin films of Example 4, Example 5, and Comparative Example 6.

FIG. 9(a) shows the measurement results of light absorption and circularly polarized dichroism spectrums (CD spectrums) of the thin films of Example 4, Example 5, and Comparative Example 6. The horizontal axis in FIG. 9(a) represents wavelength, and the vertical axis in FIG. 9(a) represents CD signal strength (CD[mdeg]=32,980×Δ absorbance (difference in absorption intensities between left-handed circularly polarized light and right-handed circularly polarized light)). The broken line in FIG. 9(a) indicates the CD spectrum of Example 4, the dotted line indicates the CD spectrum of Example 5, and the solid line indicates the CD spectrum of Comparative Example 6. The thin film of Example 4 showed a CD signal of +3,200 mdeg at 395 nm. That is, the thin film of Example 4 exhibited stronger absorption against left-handed circularly polarized light than right-handed circularly polarized light. The thin film of Example 5 showed a CD signal in the opposite direction and exhibited stronger absorption against left-handed circularly polarized light. Since the racemic thin film of Comparative Example 6 did not show a CD signal, circularly polarized light could not be discriminated. Incidentally, the anisotropy factor ($g_{CD}$) for discriminating circularly polarized light was larger than that of a two-dimensional structure and larger than a one-dimensional structure using phenylethylamine. This means that a naphthalene framework having two aromatic rings could induce a spiral of a one-dimensional structure more strongly than a benzene ring.

In addition, for example, the $g_{CD}$ value of the known layered structure described in J. Am. Chem. Soc. 2020, 142, 4206-4212 and the like was 0.002 or less, and thus it was confirmed that the thin film of the present invention had an excellent $g_{CD}$ value.

Figure 9B:
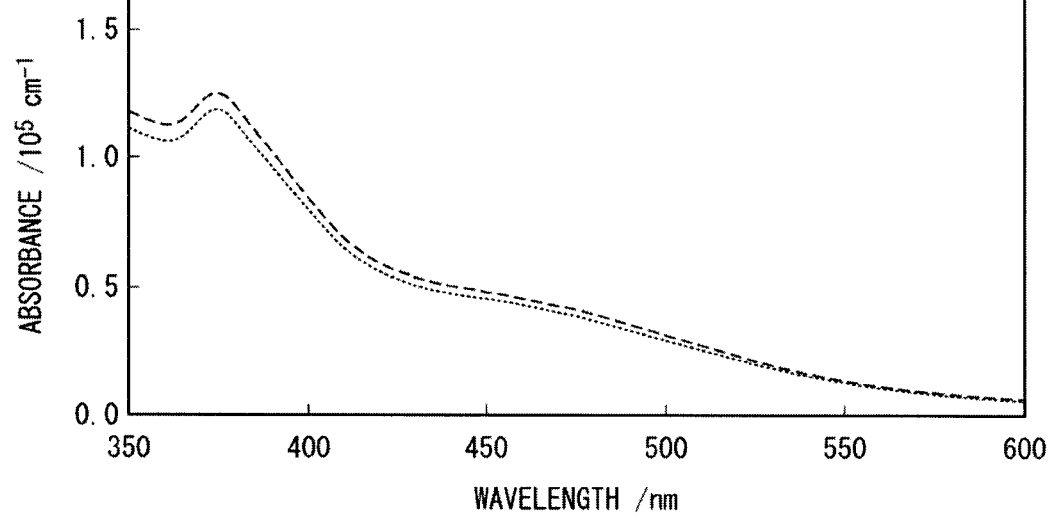

FIG. 9(b) shows the light absorption spectrum measurement results of the thin films of Example 4, Example 5, and Comparative Example 6. The horizontal axis in FIG. 9(b) represents wavelength, and the vertical axis in FIG. 9(b) represents absorbance. The broken line in FIG. 9(b) indicates the light absorption spectrum of Example 4, and the dotted line indicates the light absorption spectrum of Example 5. The thin films of Examples 4 and 5 had a peak at 395 nm. The absorption intensity per unit thickness of the thin film of Example 4 was 127,273 $cm^{-1}$. The absorption intensity per unit thickness of the thin film of Example 5 was 120,780 $cm^{-1}$. Here, the light absorption spectrum of Comparative Example 6 was the same as those of Examples 4 and 5.

FIG. 10(a) shows the results obtained by measuring circularly polarized dichroism spectrums (CD spectrums) of the thin films of Comparative Examples 8 and 9. The horizontal axis in FIG. 10(a) represents wavelength, and the vertical axis in FIG. 10(b) represents CD signal strength (CD[mdeg]=32,980×Δ absorbance (difference in absorption intensities between left-handed circularly polarized light and right-handed circularly polarized light)). The broken line in FIG. 10(a) indicates the CD spectrum of Comparative Example 8, and the dotted line indicates the CD spectrum of Comparative Example 9. The thin films of Comparative Examples 8 and 9 had a CD signal smaller than those of Examples 4 and 5 by one order. This result means that the organic halide had a strong influence on the formation of the one-dimensional spiral structure.

FIG. 9(b) shows the light absorption spectrum measurement results of the thin films of Comparative Examples 8 and 9. The horizontal axis in FIG. 9(b) represents wavelength, and the vertical axis in FIG. 9(b) represents absorbance. The broken line in FIG. 9(b) indicates the light absorption spectrum of Comparative Example 8, and the dotted line indicates the light absorption spectrum of Comparative Example 9. The thin films of Examples 4 and 5 had a peak at 395 nm. The absorption intensity per unit thickness of the thin film of Comparative Example 8 was 95,586 $cm^{-1}$.

The absorption intensity per unit thickness of the thin film of Comparative Example 9 was 96,086 cm$^{-1}$.

Figure 11:
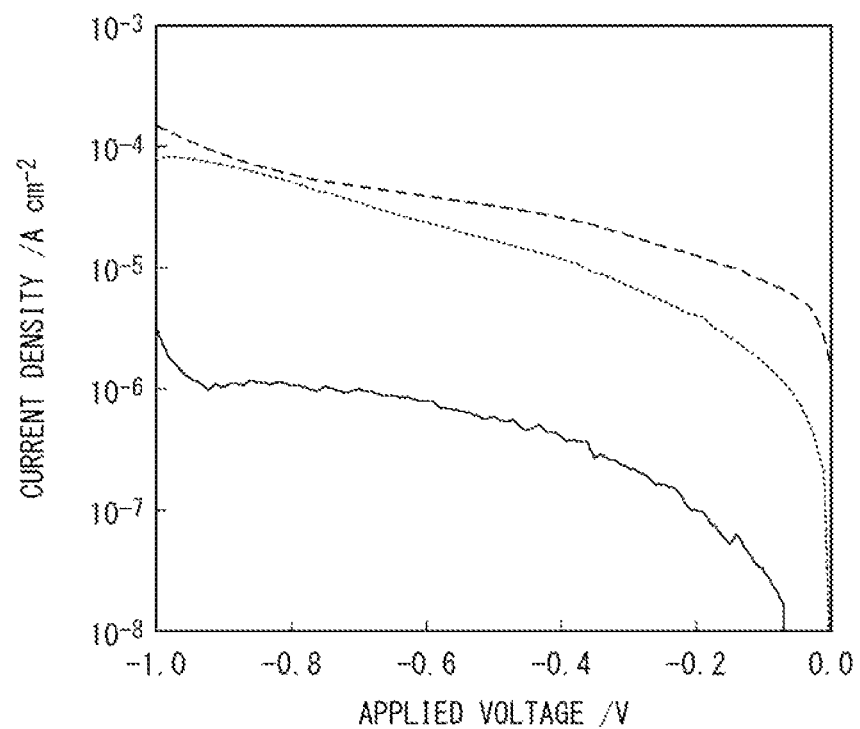
FIG. 11 is a graph showing the results obtained by measuring photocurrent and dark current characteristics for the thin film of Example 1.
Figure 12:
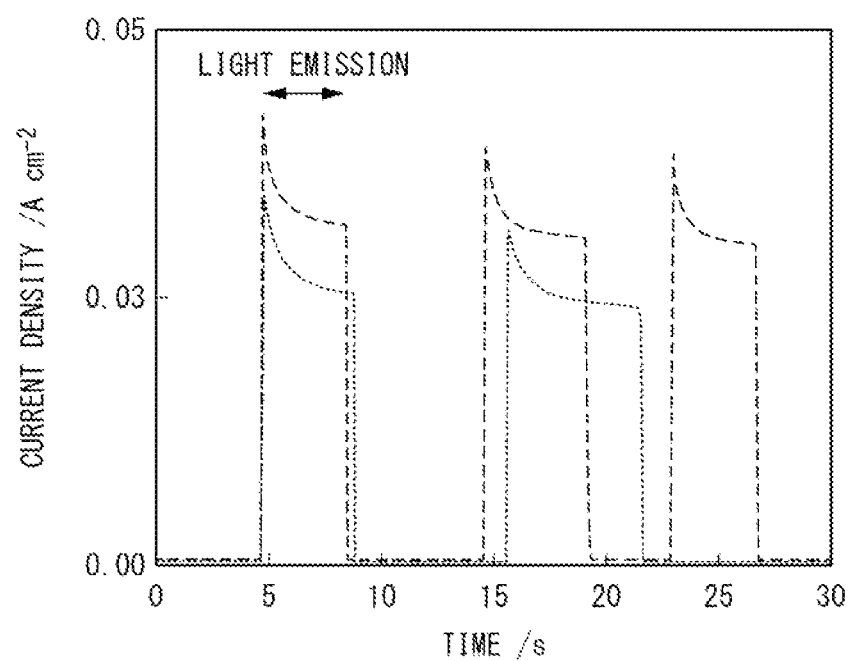
FIG. 12 is a graph showing the results obtained by measuring on-off characteristics for the thin film of Example 1.

FIGS. 11 and 12 show graphs of the results of photocurrent and dark current characteristics and on-off characteristics of the thin film obtained in Example 1.

The broken line in FIG. 11 indicates current-voltage characteristics when right-handed circularly polarized light (RCP) was emitted, the dotted line indicates current-voltage characteristics when left-handed circularly polarized light (LCP) was emitted, and the solid line indicates current-voltage characteristics of the thin film when no light was emitted (dark). The horizontal axis in FIG. 11 represents an applied voltage (V), and the vertical axis in FIG. 11 represents generated current density (A/cm$^2$).

Regardless of which circularly polarized light was emitted, a current higher than the current (dark current) when no light was emitted was generated. In addition, in Example 1, since strong absorption against right-handed circularly polarized light was exhibited, a higher current was generated when right-handed circularly polarized light was emitted than when left-handed circularly polarized light was emitted. Here, in Example 2, since strong absorption against left-handed circularly polarized light was exhibited, the result in which a higher current was generated when left-handed circularly polarized light was emitted than when right-handed circularly polarized light was emitted was obtained. The extinction ratio (the sensitivity ratio of left-handed and right-handed circularly polarized light, $R_L/R_R$) of the two-dimensional structure was 1.2. Based on these results, it was found that the thin film of the present disclosure had sufficient sensitivity to circularly polarized light and could be utilized as a circularly polarized light detection element.

The broken line in FIG. 12 indicates current on-off characteristics of the thin film when the applied voltage was 0.5 V, and right-handed circularly polarized light (RCP) was emitted, and the dotted line indicates current on-off characteristics of the thin film when left-handed circularly polarized light (LCP) was emitted. The horizontal axis in FIG. 12 represents elapsed time(s), and the vertical axis in FIG. 12 represents generated current density (A/cm$^2$).

Since the rise of the current was steep, regardless of which circularly polarized light was emitted, the thin film of the present disclosure exhibited excellent responsiveness when utilized as a circularly polarized light detection element. Here, when the same experiment was performed using the thin film of Comparative Example 7, the current leaked. This is thought to have been caused by the fact that parts of the positive electrode layer and the negative electrode layer were conductive because the surface roughness of the thin film prepared in Comparative Example 7 was large (>30 nm). That is, when the thin film was prepared in the presence of the organic halide (methylamine), the surface roughness needed for element formation could be minimized, and as a result, the leakage of the current could be minimized.

Figure 13:
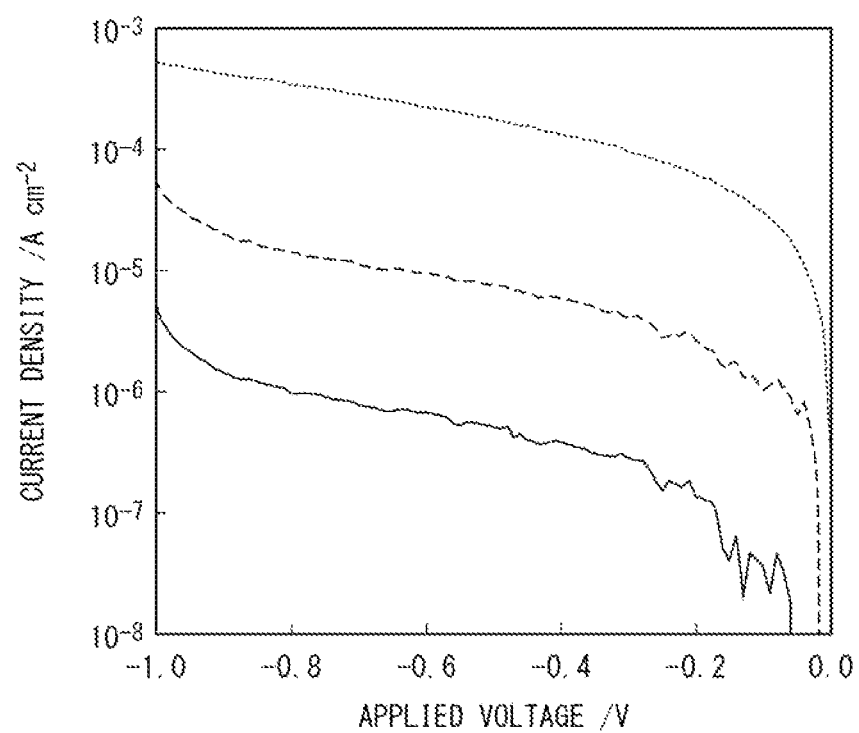
FIG. 13 is a graph showing the results obtained by measuring photocurrent and dark current characteristics for the thin film of Example 4.
Figure 14:
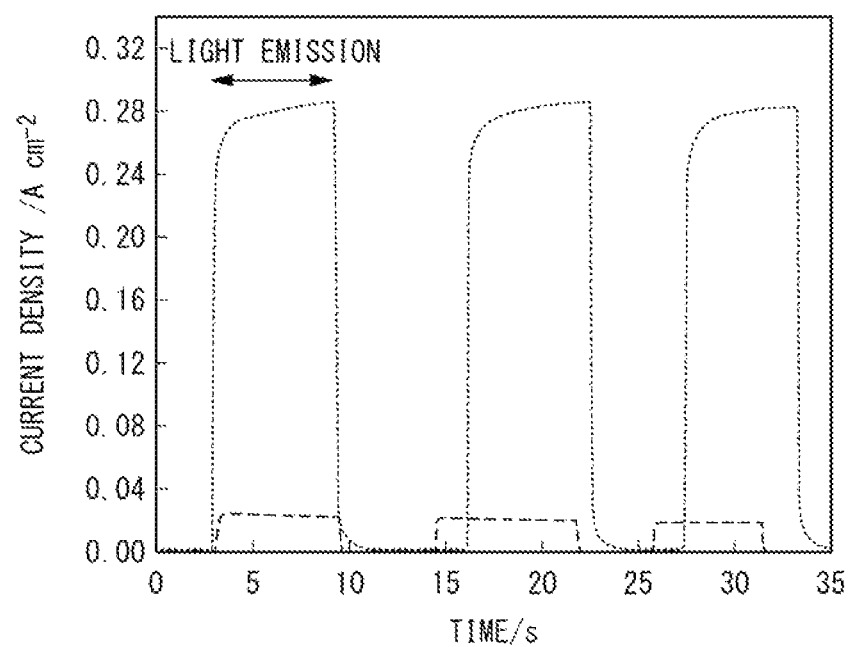
FIG. 14 is a graph showing the results obtained by measuring on-off characteristics for the thin film of Example 4.

FIG. 13 and FIG. 14 show the results of photocurrent characteristic measurement and on-off characteristic measurement of the thin film of Example 4.

The broken line in FIG. 13 indicates current-voltage characteristics of the thin film when right-handed circularly polarized light (RCP) was emitted, the dotted line indicates current-voltage characteristics of the thin film when left-handed circularly polarized light (LCP) was emitted, and the solid line indicates current-voltage characteristics of the thin film when no light was emitted (dark). The horizontal axis in FIG. 13 represents applied voltage (V), and the vertical axis in FIG. 14 represents generated current density (A/cm$^2$).

Regardless of which circularly polarized light was emitted, a current higher than the current (dark current) when no light was emitted was generated. In addition, in Example 4, since strong absorption against left-handed circularly polarized light was exhibited, a higher current was generated when left-handed circularly polarized light was emitted than when right-handed circularly polarized light was emitted. Here, in Example 5, since strong absorption against right-handed circularly polarized light was exhibited, the result in which a higher current was generated when right-handed circularly polarized light was emitted than when right-handed circularly polarized light was emitted was obtained. The extinction ratio (the sensitivity ratio of left-handed and right-handed circularly polarized light, $R_L/R_R$) of the one-dimensional structure was 25.4. Based on these results, it was found that the thin film of the present disclosure had sufficient sensitivity to circularly polarized light and could be utilized as a circularly polarized light detection element.

The broken line in FIG. 14 indicates current on-off characteristics of the thin film when the applied voltage was 0.5 V, and right-handed circularly polarized light (RCP) was emitted, and the dotted line indicates current on-off characteristics of the thin film when left-handed circularly polarized light (LCP) was emitted. The horizontal axis in FIG. 14 represents elapsed time(s), and the vertical axis in FIG. 14 represents generated current density (A/cm$^2$).

Since the rise of the current was steep regardless of which circularly polarized light was emitted, the thin film of the present invention exhibited excellent responsiveness when utilized as a circularly polarized light detection element.

REFERENCE SIGNS LIST 100, 200 Thin film
101, 201 Perovskite type substance
102 Inorganic layer
103, 203 Chiral molecule
104, 204 Boundary part
105, 205 Organic layer
106, 206 Negative electrode layer
107, 207 Positive electrode layer
108, 208 Negative electrode-side adhesive layer
109, 209 Positive electrode-side adhesive layer
110, 220 Circularly polarized light detection element
202 Inorganic chain

The invention claimed is:

1. A thin film for detecting a circularly polarized light, comprising:
  a plurality of inorganic layers constituting a layered structure and/or a plurality of inorganic chains constituting a chain structure, which are formed of a perovskite type substance; and
  chiral molecules incorporated in at least a part of a boundary part between the adjacent inorganic layers and/or between the inorganic chains,
  wherein the chiral molecules include only one of S-form chiral molecules and R-form chiral molecules, or chiral molecules with a higher abundance proportion of one of S-form chiral molecules and R-form chiral molecules than an abundance proportion of the other of the S-form chiral molecules and R-form chiral molecules, and
  wherein the crystal structure of the perovskite type substance is oriented in a predetermined direction.

2. The thin film according to claim 1,
wherein an absorption intensity per unit thickness is 50,000 cm$^{-1}$ or more and 500,000 cm$^{-1}$ or less.

3. The thin film according to claim 1,
wherein a surface roughness Ra is 1 nm or more and 30 nm or less.

4. The thin film according to claim 1,
wherein the chiral molecules form an organic layer at the boundary part, and the inorganic layer and the organic layer are alternately laminated and/or the chiral molecules surround the inorganic chains.

5. The thin film according to claim 1,
wherein the chiral molecules are fixed to the inorganic layer and/or the inorganic chain.

6. The thin film according to claim 1,
wherein the chiral molecules are bonded to the inorganic layer and/or the inorganic chain via a functional group covalently bonded to asymmetric carbon atoms constituting the chiral molecules.

7. The thin film according to claim 6,
wherein
the functional group is a substituent that is able to have a charge, and
the substituent and the perovskite type substance form a bond via a halogen ion, which fixes the chiral molecule to the inorganic layer and/or the inorganic chain.

8. The thin film according to claim 1,
wherein the perovskite type substance and the chiral molecules constitute a compound A$_2$BX$_4$ and/or ABX$_3$ composed of three types of ions A, B, and X, and
wherein the thin film includes a structure in which the ion B and the ion X form a plurality of units having an octahedron structure, and the octahedron structures of the adjacent units share one vertex and/or plane.

9. The thin film according to claim 8, comprising
a plurality of inorganic layers constituting a layered structure,
wherein the perovskite type substance and the chiral molecules constitute a compound A$_2$BX$_4$ composed of three types of ions A, B, and X, and
wherein the thin film includes a structure in which the ion B and the ion X form a plurality of units having an octahedron structure, and the octahedron structures of the adjacent units share one vertex.

10. The thin film according to claim 8, comprising
a plurality of inorganic chains constituting a chain structure,
wherein the perovskite type substance and the chiral molecules constitute a compound ABX$_3$ composed of three types of ions A, B, and X, and
wherein the thin film includes a structure in which the ion B and the ion X form a plurality of units having an octahedron structure, and the octahedron structures of the adjacent units share one plane.

11. The thin film according to claim 8,
wherein the ion A is an aromatic compound containing an ethylammonium ion, the ion B is a lead ion or a tin ion, and the ion X is a halogen ion.

12. A method for producing the thin film according to claim 1, comprising:
a first step in which a precursor of the perovskite type substance which is a raw material of the thin film, the chiral molecules, and an organic halide that is able to be sublimated by heating and reacts with some of elements constituting the perovskite type substance are dissolved in a solvent;
a second step in which a solution obtained in the first step is applied onto a substrate using a spin coating method to form an untreated coating film on the substrate; and
a third step in which the untreated coating film is heated to sublimate the organic halide contained in the untreated coating film.

13. The method for producing a thin film according to claim 12,
wherein the precursor of the perovskite type substance is a lead halide, and
wherein the organic halide is methylammonium halide or formamidinium halide.

14. The method for producing a thin film according to claim 13,
wherein a halogen atom contained in the lead halide and the organic halide is any of a bromine atom, a chlorine atom, and an iodine atom.

15. A circularly polarized light detection element comprising the thin film according to claim 1.

16. The circularly polarized light detection element according to claim 15,
wherein a negative electrode layer, the thin film, and a positive electrode layer are laminated in that order, and at least one of the negative electrode layer and the positive electrode layer has light transmitting properties.

17. A device into which the circularly polarized light detection element according to claim 15 is incorporated.

18. A method for inducing an R- or S-arranged chiral structure for a perovskite structure of a perovskite type substance including a plurality of inorganic layers constituting a layered structure and/or a plurality of inorganic chains constituting a chain structure, the method comprising
a step in which only one of S-form chiral molecules and R-form chiral molecules or chiral molecules with a higher abundance proportion of one of S-form chiral molecules and R-form chiral molecules than an abundance proportion of the other of S-form chiral molecules and R-form chiral molecules are incorporated in at least a part of a boundary part between the adjacent inorganic layers and/or between the inorganic chains contained in the perovskite type substance so that the crystal structure of the perovskite type substance is oriented in a predetermined direction.

19. A thin film formed of a perovskite type substance and imparted with chirality,
wherein the thin film includes a plurality of inorganic layers constituting a layered structure and/or a plurality of inorganic chains constituting a chain structure, and
only one of S-form chiral molecules and R-form chiral molecules, or
chiral molecules with a higher abundance proportion of one of S-form chiral molecules and R-form chiral molecules than an abundance proportion of the other of S-form chiral molecules and R-form chiral molecules which are incorporated in at least a part of a boundary part between the adjacent inorganic layers and/or between the inorganic chains, and
wherein the crystal structure of the perovskite type substance is oriented in a predetermined direction.

* * * * *